(12) United States Patent
Nag et al.

(10) Patent No.: US 7,521,466 B2
(45) Date of Patent: Apr. 21, 2009

(54) DIPEPTIDE PHENYL ETHERS

(75) Inventors: Bishwajit Nag, Union City, CA (US); Abhijeet Nag, Fremont, CA (US); Debendranath Dey, Fremont, CA (US); Partha Neogi, Fremont, CA (US); Shiv Kumar Agarwal, Chennai (IN); Surendra Kumar Pandey, Chennai (IN)

(73) Assignee: Bexel Pharmaceuticals, Inc., Union City, CA (US)

( * ) Notice: Subject to any disclaimer, the term of this patent is extended or adjusted under 35 U.S.C. 154(b) by 141 days.

(21) Appl. No.: 11/429,015

(22) Filed: May 4, 2006

(65) Prior Publication Data

US 2007/0037863 A1 Feb. 15, 2007

Related U.S. Application Data

(62) Division of application No. 10/681,827, filed on Oct. 7, 2003, now Pat. No. 7,087,576.

(51) Int. Cl.
*A01N 43/82* (2006.01)
*C07D 277/00* (2006.01)

(52) U.S. Cl. ....................... 514/369; 548/182
(58) Field of Classification Search ........................ None
See application file for complete search history.

(56) References Cited

U.S. PATENT DOCUMENTS

| | | | |
|---|---|---|---|
| 5,166,137 | A | 11/1992 | Otterlei et al. |
| 5,441,971 | A | 8/1995 | Sohda et al. |
| 5,527,546 | A | 6/1996 | Penza et al. |
| 6,004,813 | A | 12/1999 | Surlupi-Crescenzi et al. |
| 6,147,100 | A | 11/2000 | Seno et al. |
| 6,316,465 | B1 | 11/2001 | Pershadsingh et al. |
| 6,331,633 | B1 | 12/2001 | Neogi et al. |
| 6,515,003 | B1 | 2/2003 | Pfahl et al. |
| 6,552,058 | B1 | 4/2003 | Sohda et al. |
| 6,562,849 | B1 | 5/2003 | Fujita et al. |
| 6,617,339 | B1 | 9/2003 | Gravestock |
| 6,620,830 | B2 | 9/2003 | Chiang |
| 6,664,281 | B1 | 12/2003 | Tajima |
| 6,667,328 | B2 | 12/2003 | Yoneda et al. |
| 6,680,387 | B2 | 1/2004 | Druzgala et al. |
| 6,686,475 | B2 | 2/2004 | Hindley |
| 6,699,896 | B1 | 3/2004 | Malamas |
| 6,706,746 | B2 | 3/2004 | Fujita et al. |
| 6,730,687 | B1 | 5/2004 | Miyachi et al. |
| 6,765,013 | B2 | 7/2004 | Pfahl et al. |
| 6,794,401 | B2 | 9/2004 | Nag et al. |
| 7,087,576 | B2 | 8/2006 | Nag et al. |
| 2003/0229120 | A1 | 12/2003 | Olsen et al. |
| 2005/0288341 | A1 | 12/2005 | Nag et al. |
| 2006/0247285 | A1* | 11/2006 | Neogi et al. ............ 514/369 |

FOREIGN PATENT DOCUMENTS

| | | |
|---|---|---|
| EP | 1 148 054 A1 | 10/2001 |
| EP | 1 213 287 A1 | 6/2002 |
| JP | 2001-308814 | 6/2002 |
| WO | WO 00/64888 | 2/2000 |
| WO | WO 01/02377 | 11/2001 |
| WO | WO 03/027081 | 4/2003 |
| WO | WO 2004/066964 | 8/2004 |
| WO | WO 2004/080480 | 9/2004 |
| WO | WO 2005/034981 | 4/2005 |
| WO | WO 2006/089225 | 8/2006 |

OTHER PUBLICATIONS

Schatz et al. Why Can't We Prevent Type 1 Diabetes. Diabetes Care, Dec. 2003, vol. 26, No. 12, pp. 3326-3328.*
National Diabetes Face Sheet. http://www.cdc.gov/diabetes/pubs/general.htm. Accessed online Apr. 7, 2008; pp. 1-4.*
International Search Report from corresponding International Application No. PCT/US2004/000790, issued Jan. 3, 2005.
International Written Opinion, PCT/US2004/000790. Issued Jan. 3, 2005.
International Search Report from corresponding International Application No. PCT/US2006/005846, issued Jun. 22, 2006.
International Written Opinion, PCT/US2006/005846, Issued Jun. 22, 2006.
International Search Report from corresponding International Application No. PCT/US04/32931, issued Feb. 11, 2005.
International Written Opinion from International Application No. PCT/US04/32931, issued Feb. 11, 2005.
Derivative: Definition. Accessed online on Oct. 18, 2005 at http://www.answers.com/derivative. 1 pg.
Analogue: Definition. Accessed online Oct. 18, 2005 at http://www.answers.com/analogue. 1 pg.
Arend et al., Arthitis Rheum, 38:151-60,1995.
Brennan et al., Brennan et al., Inhibitory effect of TNFα Antibodies on Synovial Cell Interleukin-1 Production in Rheumatoid Arthitis, Lancet, vol. 334:244-7, 1989.
Goldenberg, Clin Ther, 21:75-87, 1999.
Haworth et al., Eur J Immunol, 21:2575-79, 1991.
Luong et al., Ann Pharmacother, 34:743-60, 2000.
Moser et al., J Clin Invest, 83:444-55,1989.
Georgian Office Action, dated Dec. 27, 2006, from corresponding Georgian Application No. AP2004008942.
China Office Action, dated Oct. 20, 2006, from corresponding Chinese Application No. 200480006737.9.
Singapore Second Written Opinion, dated Mar. 9, 2007, from corresponding Japanese Application No. 200504369-0.
European Search Report from corresponding European Application No. 04701752.0 Issued Jun. 1, 2007.

* cited by examiner

*Primary Examiner*—Cecilia Tsang
*Assistant Examiner*—Marcela M Cordero Garcia
(74) *Attorney, Agent, or Firm*—Weaver Austin Villeneuve & Sampson LLP

(57) ABSTRACT

Novel dipeptide ethers are effective for lowering blood glucose, serum insulin, free fatty acids, cholesterol and triglyceride levels. The dipeptide ethers are also useful for the treatment and/or prophylaxis of diabetes, obesity, inflammation and autoimmune diseases such as multiple sclerosis and rheumatoid arthritis.

17 Claims, 8 Drawing Sheets

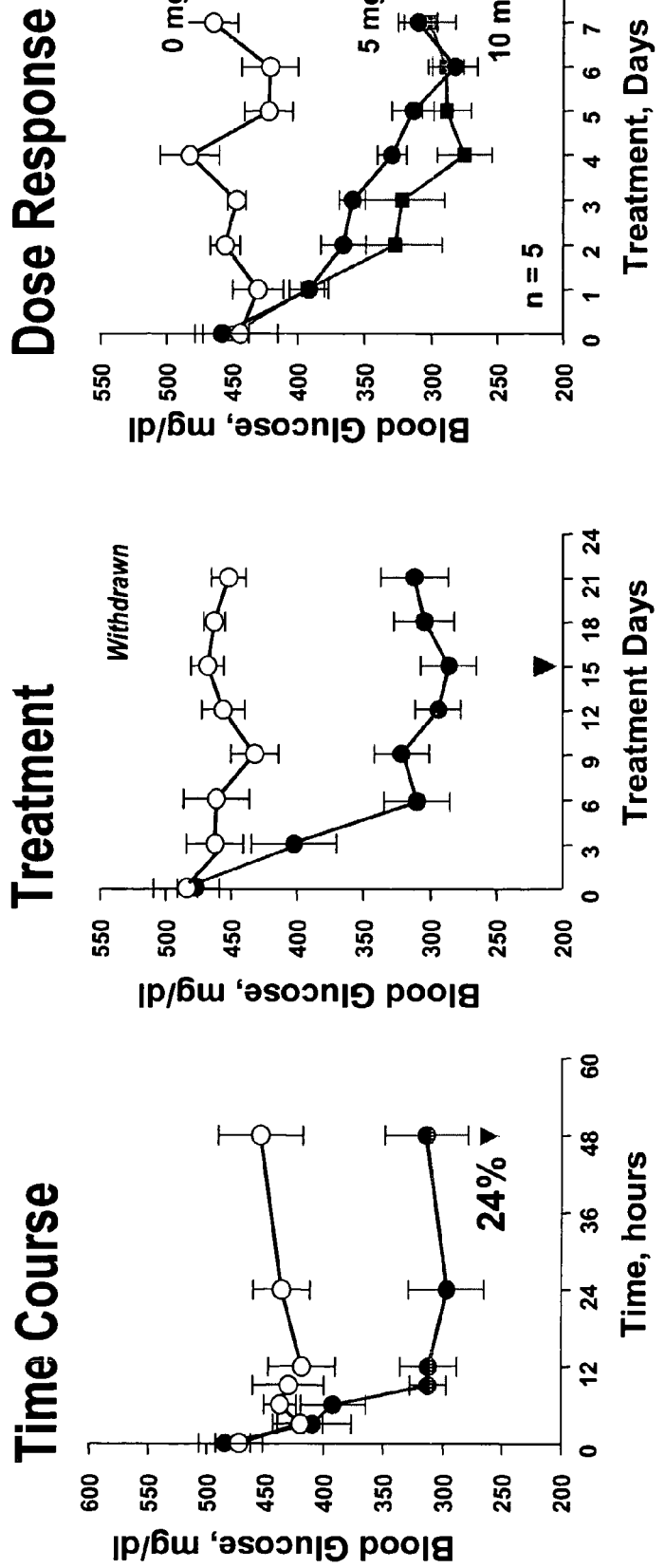

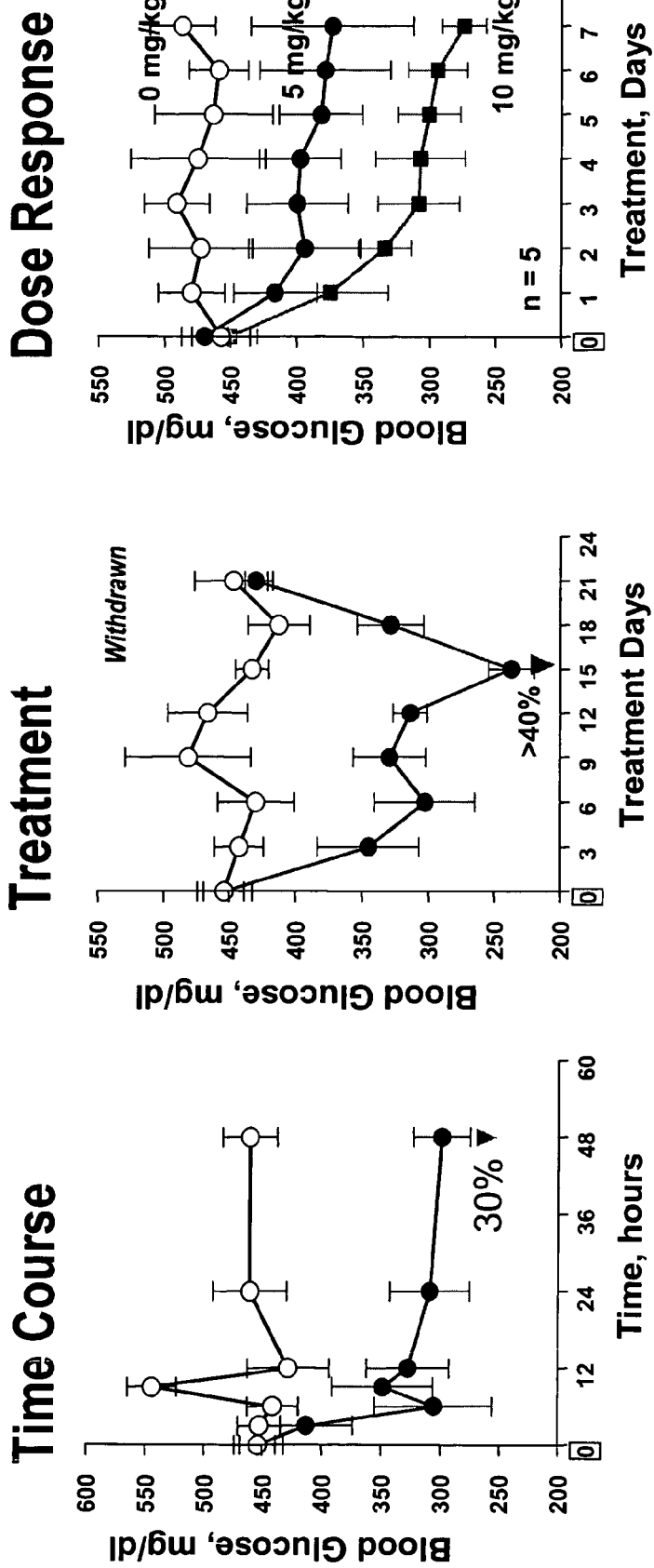

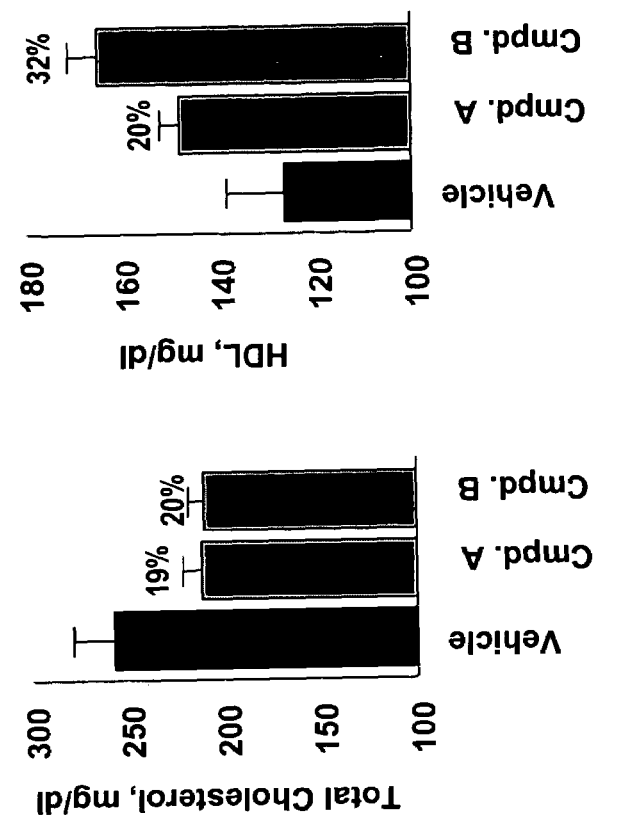
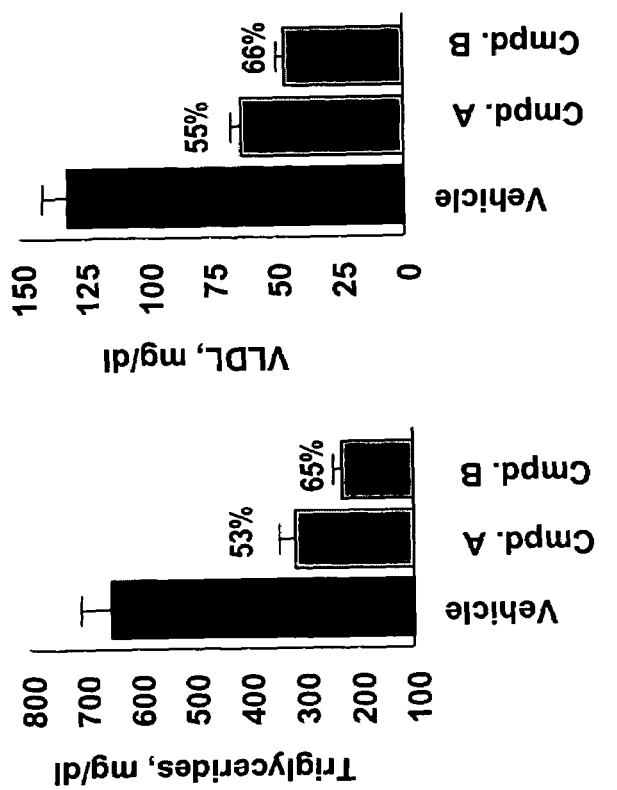
FIG. 4A FIG. 4B FIG. 4C FIG. 4D

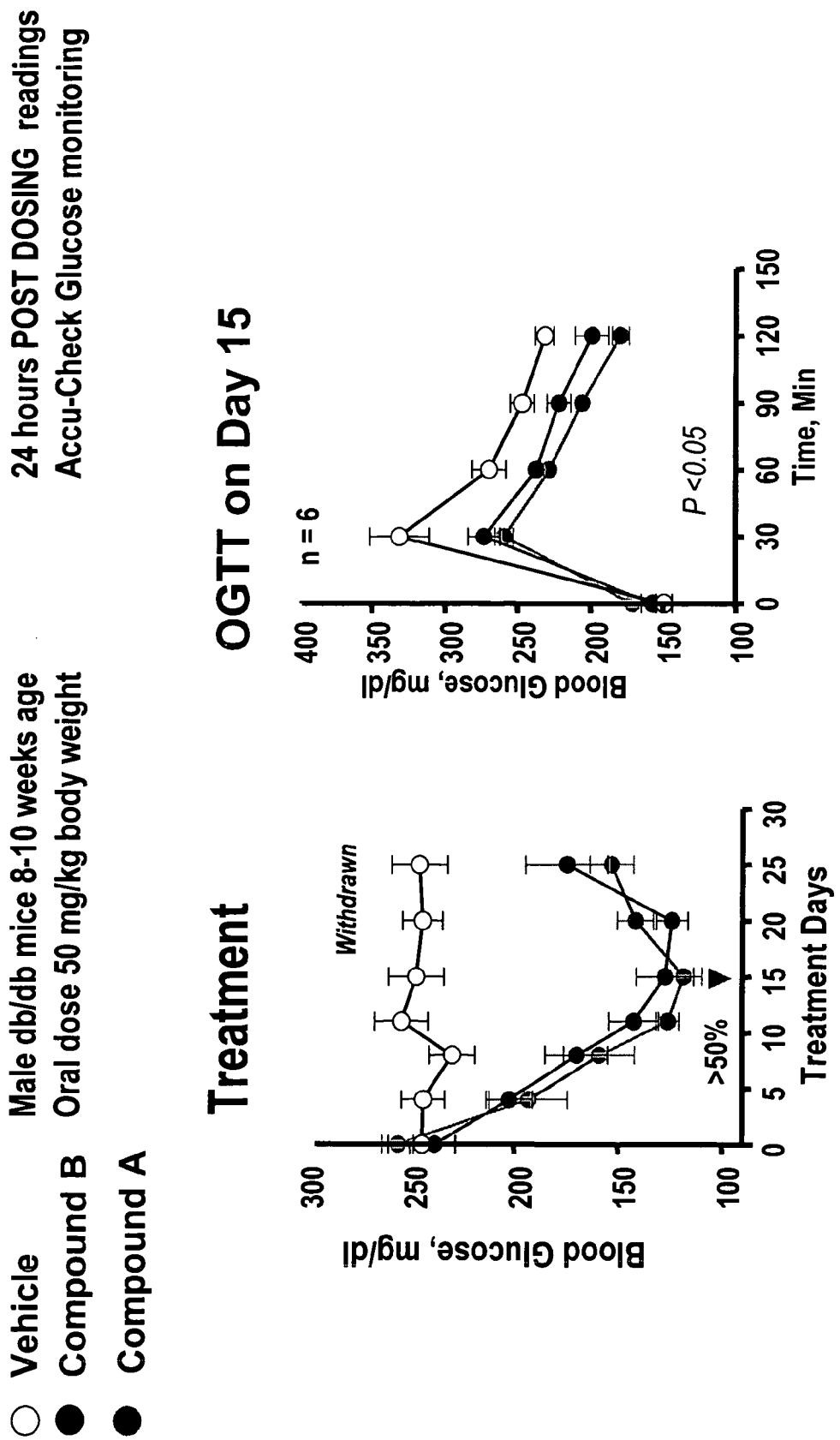

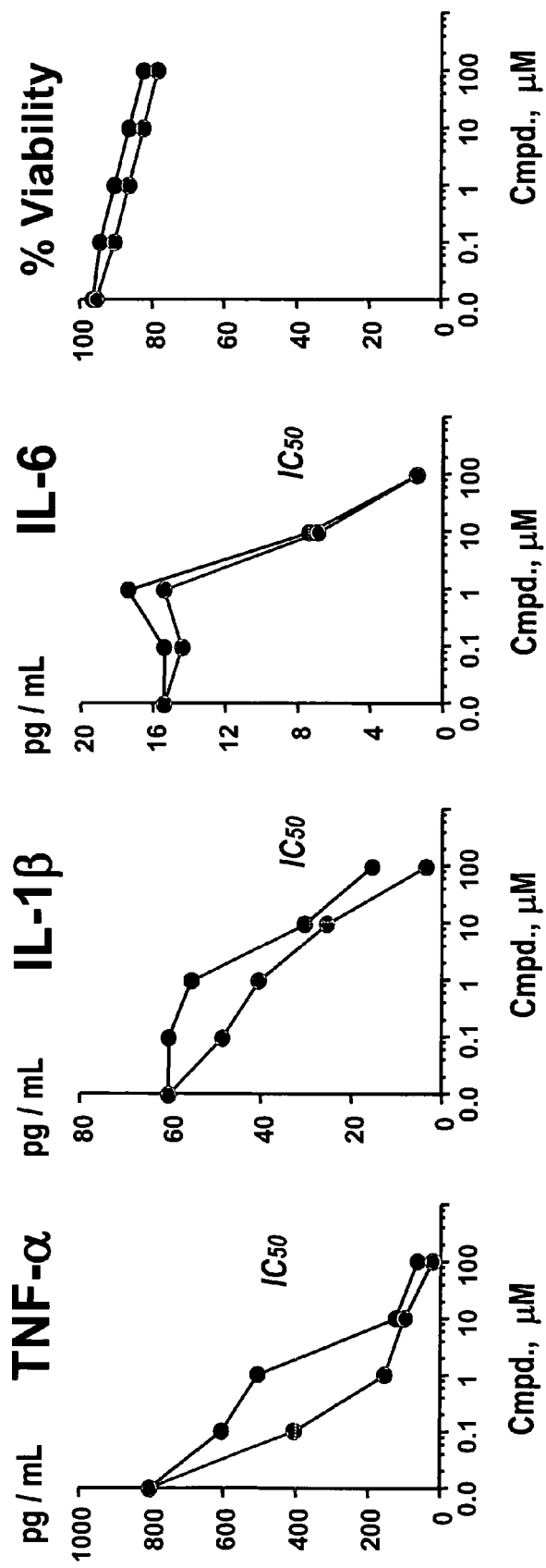

DIPEPTIDE PHENYL ETHERS

RELATED APPLICATION DATA

This is a divisional of prior application Ser. No. 10/681,827, filed Oct. 7, 2003 now U.S. Pat. No. 7,087,576 entitled, "DIPEPTIDE PHENYL ETHERS" by Bishwajit Nag, Abhijeet Nag, Debendranath Dey, Partha Neogi, Shiv Kumar Agarwal and Surendra Kumar Pandey, and is incorporated herein by reference. This invention is also related to U.S. patent application Ser. No. 10/356,113, Filed Jan. 31, 2003, naming Bishwajit Nag, Abhijeet Nag, Shiv Kumar Agarwal, and Debendranath Dey as inventors, and entitled "Amino Acid Phenoxy Ethers." That application is incorporated herein by reference in its entirety and for all purposes.

FIELD OF THE INVENTION

The present invention relates to novel dipeptide phenyl ethers of formula (I), their derivatives, their analogs, their tautomeric forms, their stereoisomers, their polymorphs, their pharmaceutically acceptable salts, their pharmaceutically acceptable solvates and pharmaceutically acceptable compositions containing them.

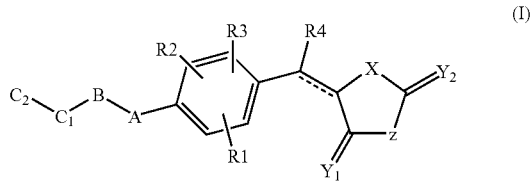

(I)

The present invention also relates to a process for the preparation of the above said novel compounds, their analogs, their derivatives, their tautomeric forms, their stereoisomers, their polymorphs, their pharmaceutically acceptable salts, pharmaceutically acceptable solvates, novel intermediates and pharmaceutical compositions containing them.

The compounds of the present invention are effective in lowering blood glucose, serum insulin, free fatty acids, cholesterol and triglyceride levels and are useful in the treatment and/or prophylaxis of type II diabetes. The compounds of the present invention are effective in treatment of obesity, inflammation, autoimmune diseases such as such as multiple sclerosis and rheumatoid arthritis. Surprisingly, these compounds increase the leptin level and have no liver toxicity.

Furthermore, the compounds of the present invention are useful for the treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines such as TNF-α, IL-1, IL-6, IL-1β and cyclooxygenase such as COX-2.

BACKGROUND OF THE INVENTION

The causes of type I and II diabetes are not yet clear, although both genetics and environment seem to be the factors. Type I is an autonomic immune disease and patient must take insulin to survive. Type II diabetes is more common form, is metabolic disorder resulting from the body's inability to make a sufficient amount of insulin or to properly use the insulin that is produced. Insulin secretion and insulin resistance are considered the major defects, however, the precise genetic factors involved in the mechanism remain unknown.

Patients with diabetes usually have one or more of the following defects:

Less secretion of insulin by the pancreas;

Over production of glucose by the liver;

Independent of the glucose uptake by the skeletal muscles;

Defects in glucose transporters, desensitization of insulin receptors; and

Defects in the metabolic breakdown of polysaccharides.

Other than the parenteral or subcutaneous administration of insulin, there are four major classes of oral hypoglycemic agents used i.e sulfonylurea, biguanides, alpha glucosidase inhibitors and thiazolidinediones.

Each of the current agents available for use in treatment of diabetes has certain disadvantages. Accordingly, there is a continuing interest in the identification and development of new agents, which c an be orally administered, for use in the treatment of diabetes.

The thiazolidinedione class listed above has gained more widespread use in recent years for treatment of type II diabetes, exhibiting particular usefulness as insulin sensitizers to combat "insulin resistance", a condition in which the patient becomes less responsive to the effects of insulin. There is a continuing need for nontoxic, more widely effective insulin sensitizers.

Recent advances in scientific understanding of the mediators involved in acute and chronic inflammatory diseases and cancer have led to new strategies in the search for effective therapeutics. Traditional approaches include direct target intervention such as the use of specific antibodies, receptor antagonists, or enzyme inhibitors. Recent breakthroughs in the elucidation of regulatory mechanisms involved in the transcription and translation of a variety of mediators have led to increased interest in therapeutic approaches directed at the level of gene transcription.

As indicated above, the present invention is also concerned with treatment of immunological diseases or inflammation, notably such diseases as are mediated by cytokines or cyclooxygenase. The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and providing the necessary "help" for T cell stimulation and proliferation. Most importantly macrophages make IL-1, IL-12 and TNF-α all of which are potent pro-inflammatory molecules and also provide help for T cells. In addition, activation of macrophages results in the induction of enzymes, such as cyclooxygenase II (COX-2), inducible nitric oxide synthase (iNOS) and production of free radicals capable of damaging normal cells. Many factors activate macrophages, including bacterial products, superantigens and interferon gamma (IFNγ). It is believed that phosphotyrosine kinases (PTKs) and other undefined cellular kinases are involved in the activation process.

Cytokines are molecules secreted by immune cells that are important in mediating immune responses. Cytokine production may lead to the secretion of other cytokines, altered cellular function, cell division or differentiation. Inflammation is the body's normal response to injury or infection. However, in inflammatory diseases such as rheumatoid arthritis, pathologic inflammatory processes can lead to morbidity and mortality. The cytokine tumor necrosis factor-alpha (TNF-α) plays a central role in the inflammatory response and has been targeted as a point of intervention in inflammatory disease. TNF-α is a polypeptide hormone released by activated macrophages and other cells. At low concentrations, TNF-α participates in the protective inflammatory response by activating leukocytes and promoting their migration to extravascular sites of inflammation (Moser et al., J Clin Invest, 83:444-55, 1989). At higher concentrations, TNF-α can act as a potent pyrogen and induce the production of other pro-inflammatory cytokines (Haworth et al., Eur J Immunol, 21:2575-79, 1991; Brennan et al., Lancet, 2:244-7, 1989). TNF-α also stimulates the synthesis of acute-phase proteins. In rheumatoid arthritis, a chronic and progressive inflammatory disease affecting about 1% of the adult U.S. population, TNF-α mediates the cytokine cascade that leads to joint damage and destruction (Arend et al., Arthritis Rheum, 38:151-60, 1995). Inhibitors of TNF-α, including soluble TNF receptors (etanercept) (Goldenberg, Clin Ther, 21:75-87, 1999) and anti-TNF-α antibody (infliximab) (Luong et al., Ann Pharmacother, 34:743-60, 2000), have recently been approved by the U.S. Food and Drug Administration (FDA) as agents for the treatment of rheumatoid arthritis.

Elevated levels of TNF-α have also been implicated in many other disorders and disease conditions, including cachexia, septic shock syndrome, osteoarthritis, inflammatory bowel disease such as Crohn's disease and ulcerative colitis etc.

It can be seen that inhibitors of TNF-α are potentially useful in the treatment of a wide variety of diseases. Compounds that inhibit TNF-α have been described in several patents.

Excessive production of IL-6 is implicated in several disease states, it is highly desirable to develop compounds that inhibit IL-6 secretion. Compounds that inhibit IL-6 have been described in U.S. Pat. Nos. 6,004,813; 5,527,546 and 5,166,137.

The cytokine IL-1β also participates in the inflammatory response. It stimulates thymocyte proliferation, fibroblast growth factor activity, and the release of prostaglandin from synovial cells.

Elevated or unregulated levels of the cytokine IL-1β have been associated with a number of inflammatory diseases and other disease states, including but not limited to adult respiratory distress syndrome, allergy, Alzheimer's disease etc. Since overproduction of IL-1β is associated with numerous disease conditions, it is desirable to develop compounds that inhibit the production or activity of IL-1β.

It will be appreciated from the foregoing facts that, while there have been extensive prior efforts to provide compounds for inhibiting, for example, TNF-α, IL-1, IL-6, COX-2 or other agents considered responsible for immune response, inflammation or inflammatory diseases, e.g. arthritis, there still remains a need for new and improved compounds for effectively treating or inhibiting such diseases.

With an objective of providing compounds, which are effective for such treatments as well as for the treatment of, for example, insulin resistance, hyperlipidemia, obesity, inflammation, multiple sclerosis and arthritis, we have continued our research to develop new thiazolidinediones.

An objective of the present invention is to provide novel dipeptide phenyl ether compounds, their derivatives, their analogs, their tautomeric forms, their stereoisomers, their polymorphs, their pharmaceutically acceptable salts, their pharmaceutically acceptable solvates and pharmaceutical compositions containing them or their mixtures that are useful for treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines such as TNF-α, IL-1, IL-6, IL-1β and cyclooxygenase such as COX-2.

Another objective of the present invention is to provide novel dipeptide phenyl ether compounds, their derivatives, their analogs, their tautomeric forms, their stereoisomers, their polymorphs, their pharmaceutically acceptable salts, their pharmaceutically acceptable solvates and pharmaceutical compositions containing them or their mixtures having enhanced activities, with little or no toxic effect.

Yet another objective of the present invention is to provide a process for the preparation of novel dipeptide phenyl ether compounds of formula (I), their derivatives, their analogs, their tautomeric forms, their stereoisomers, their polymorphs, their pharmaceutically acceptable salts and their pharmaceutically acceptable solvates.

SUMMARY OF THE INVENTION

The present invention, relates to novel dipeptide phenyl ethers of formula (I)

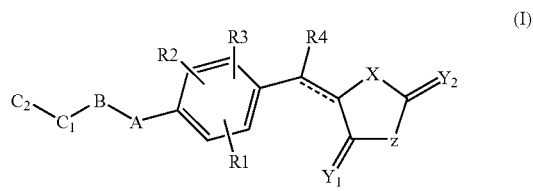

their derivatives, their analogs, their tautomeric forms, their stereoisomers, their polymorphs, their pharmaceutically acceptable salts, their pharmaceutically acceptable solvates, wherein —— represents an optional double bond; X and Z may be same or different and independently represent oxygen, sulfur or $NR_5$, wherein $R_5$ represents hydrogen or linear or branched alkyl group provided both X and Z are not same when they represent oxygen or sulfur; $Y_1$ and $Y_2$ may be same or different and independently represent oxygen, sulfur or $NR_5$, wherein $R_5$ represents hydrogen or linear or branched alkyl group; $R_1$, $R_2$, $R_3$ and $R_4$ may be same or different and independently represent hydrogen, halogen, hydroxy, nitro, cyano, formyl, mono-, di-, or unsubstituted amino, linear or branched alkyl, linear or branched alkoxy group; A represents oxygen, sulfur or NR, wherein R represents hydrogen or linear or branched alkyl; B represents a bond or substituted or unsubstituted aryl, heterocyclyl or heteroaryl ring of 5 to 14 carbon and hetero atoms; $C_1$ and $C_2$ may be same or different and independently represent an amino acid or a derivative thereof and are linked through —NH— of $C_1$ and —CO— of $C_2$, or through —CO— of $C_1$ and —NH— of $C_2$; B is directly linked or linked through alkyl or alkylene groups of 1 to 4 carbon atoms to the α carbon of $C_1$.

BRIEF DESCRIPTION OF FIGURES

FIGS. 1A-C show the time course (FIG. 1A) of Compound B lowering blood glucose levels in db/db mice at a dose of 50 mg/kg body weight (FIG. 1B) and at 5 and 10 mg/kg body weight (FIG. 1C).

FIGS. 2A-C show the time course (FIG. 2A) of Compound A lowering blood glucose levels in db/db mice at a dose of 50 mg/kg body weight (FIG. 2B) and at 5 and 10 mg/kg body weight (FIG. 2C).

FIGS. 4A-D show the effect of Compound B on lipid profiles.

FIGS. 5A-B show the effect of Compounds A and B in ob/ob mice.

FIGS. 8A-D show the effect of Compounds A and B in LPS induced cytokine production.

DETAILED DESCRIPTION OF THE INVENTION

Figure 3A:
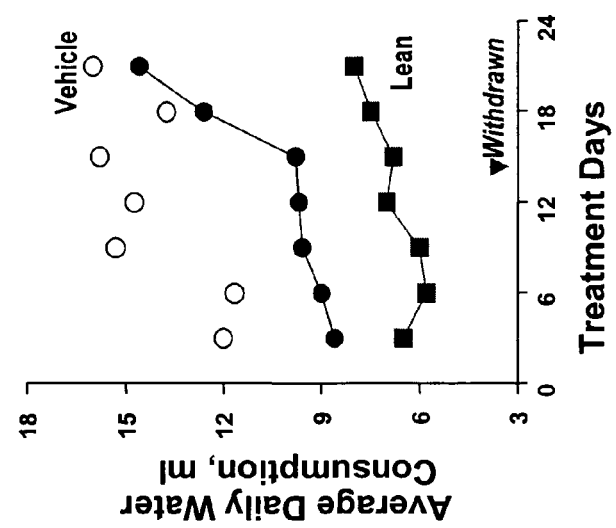
FIGS. 3A-C show Compound B lowering bodyweight gain (FIG. 3A), altering food intake (FIG. 3B) and altering water intake ( )(Fig. 3C) in obese db/db mice.

In an embodiment of the present invention, the groups represented by $R_1$, $R_2$, $R_3$ and $R_4$ are selected from hydrogen, halogen such as fluorine, chlorine, bromine or iodine; hydroxy, nitro, cyano, formyl, mono-, di-, or unsubstituted amino, linear or branched, substituted or unsubstituted ($C_1$-$C_{12}$)alkyl group such as methyl, ethyl, propyl, isopropyl, n-butyl, isobutyl, t-butyl, pentyl, hexyl, octyl, nonyl and the like; substituted or unsubstituted ($C_1$-$C_{12}$)alkoxy group such as methoxy, ethoxy, propoxy, butoxy and the like; mono-, di-, or unsubstituted amido; carboxy or carboxylic acid esters.

Suitable groups represented by R and $R_5$ are selected from hydrogen or linear branched ($C_1$-$C_6$)alkyl groups such as methyl, ethyl, propyl, isopropyl, n-butyl, isobutyl, t-butyl, pentyl, hexyl and the like.

In an embodiment of the present invention, the group represented by B is selected from aryl groups such as phenyl, naphthyl, and the like; heteroaryl rings such as pyridyl, pyrrolyl, thiazolyl, indolyl, imidazolyl, furyl and the like; heterocyclyl ring such as piperazine, morpholine, piperidine, pyrrolidine and the like. The group B may be mono-, di- or tri-substituted with substituents selected from halogen, hydroxy, nitro, cyano, formyl, mono-, di- or unsubstituted amino, linear or branched ($C_1$-$C_6$) alkyl, linear or branched ($C_1$-$C_6$) haloalkyl, linear or branched ($C_1$-$C_6$) alkoxy, linear or branched ($C_1$-$C_6$) haloalkoxy and the like; linear or branched ($C_1$-$C_6$) alkylene, linear or branched ($C_1$-$C_6$) haloalkylene and the like.

In an embodiment of the present invention, the amino acids represented by $C_1$ and $C_2$ are selected from alanine, glycine, arginine, asparagine, cysteine, cystine, glutamic acid, glutamine, histidine, isoleucine, leucine, lysine, methionine, ornithine, proline, serine, threonine, tryptophan, tyrosine and the like, which may be substituted or unsubstituted and their derivatives such as ester and amides of carboxylic acid, α-amino and side chain substituted derivatives, such as substitutions with conventional N, S, O protecting groups. The substituents include halogen, linear or branched ($C_1$-$C_6$) alkyl, linear or branched ($C_1$-$C_6$) alkylene, linear or branched ($C_1$-$C_6$) alkoxy, ($C_5$-$C_{14}$) aryl, heteroaryl, substituted or unsubstituted amino, nitro and the like.

A class of compounds includes those in which $C_1$ and $C_2$ are linked through —NH— of $C_1$ and —CO— of $C_2$. The amino acid $C_1$ is preferably tyrosine or a derivative thereof. The amino acid $C_2$ is preferably histidine, proline or derivatives thereof.

Another class of compounds includes those in which $C_1$ and $C_2$ are linked through —CO— of $C_1$ and —NH— of $C_2$. The amino acid $C_1$ is preferably tyrosine or a derivative thereof.

As used in the present specification, the following words and phrases are generally intended to have the meanings as set forth below, except to the extent that the context in which they are used indicates otherwise.

"Alkyl" is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. More preferred alkyl groups are those of $C_{13}$ or below. Still more preferred alkyl groups are those of $C_6$ and below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like.

"Alkylene" is another subset of alkyl, referring to the same residues as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkoxy" or "alkoxyl" refers to the group —O-alkyl, preferably including from 1 to 6 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

The term "amino" refers to the group —$NH_2$. The term "substituted amino" refers to the mono- or di-substituted group —NHR or —NRR where each R is independently selected from the group: optionally substituted alkyl, optionally substituted alkoxy, optionally substituted amino, optionally substituted aryl, optionally substituted heteroaryl, optionally substituted heterocyclyl, acyl, alkoxycarbonyl, sulfanyl, sulfinyl and sulfonyl, e.g., diethylamino, methylsulfonylamino, furanyl-oxy-sulfonamino.

"Aryl" and "heteroaryl" mean a 5-, 6- or 7-membered aromatic or heteroaromatic ring containing 0-4 heteroatoms selected from O, N or S; a bicyclic 9- or 10-membered aromatic or heteroaromatic ring system containing 0-4 (or more) heteroatoms selected from O, N or S; or a tricyclic 12- to 14-membered aromatic or heteroaromatic ring system containing 0-4 (or more) heteroatoms selected from O, N or S. The aromatic 6- to 14-membered aromatic carbocyclic rings include, e.g., phenyl, naphthalene, indane, tetralin, and fluorene and the 5- to 10-membered aromatic heterocyclic rings include, e.g., imidazole, oxazole, isoxazole, oxadiazole, pyridine, indole, thiophene, benzopyranone, thiazole, furan, benzimidazole, quinoline, isoquinoline, quinoxaline, pyrimidine, pyrazine, tetrazole and pyrazole.

"Halogen" or "halo" refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heterocycle" means a cycloalkyl residue of 5 to 14 carbon atoms in which one to four of the carbons is replaced by a heteroatom such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, oxadiazole, dioxane, tetrahydrofuran and the like.

"Substituted-" alkyl, aryl, heteroaryl and heterocyclyl refer respectively to alkyl, aryl, heteroaryl and heterocyclyl wherein one or more (up to about 5, preferably up to about 3) hydrogen atoms are replaced by a substituent independently selected from the group: optionally substituted alkyl (e.g., fluoroalkyl), optionally substituted alkoxy, alkylenedioxy (e.g. methylenedioxy), optionally substituted amino (e.g., alkylamino and dialkylamino), optionally substituted amidino, optionally substituted aryl (e.g., phenyl), optionally substituted aralkyl (e.g., benzyl), optionally substituted aryloxy (e.g., phenoxy), optionally substituted aralkoxy (e.g., benzyloxy), carboxy (—COOH), carboalkoxy (i.e., acyloxy or —OOCR), carboxyalkyl (i.e., esters or —COOR), carboxamido, aminocarbonyl, benzyloxycarbonylamino (CBZ-amino), cyano, carbonyl, halogen, hydroxy, optionally substituted heteroaryl, optionally substituted heteroaralkyl, optionally substituted heteroaryloxy, optionally substituted heteroaralkoxy, nitro, sulfanyl, sulfinyl, sulfonyl, and thio.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns that are sterically impractical, synthetically non-feasible and/or inherently unstable.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)- isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "therapeutically effective amount" or "effective amount" refers to that amount of a compound that is sufficient to effect treatment, as defined below, when administered to a mammal including humans, in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can readily be determined by one of ordinary skill in the art.

The term "treatment" or "treating" means any treatment of a disease in a mammal, including:

a) preventing the disease, that is, causing the clinical symptoms of the disease not to develop;

b) inhibiting the disease, that is, slowing or arresting the development of clinical symptoms; and/or c) relieving the disease, that is, causing the regression of clinical symptoms.

The active compounds according to the present invention may be administered by any suitable route, including orally, parenterally, by inhalation spray, rectally, or topically in dosage unit formulations containing conventional pharmaceutically acceptable carriers, adjuvants, and vehicles. The term "parenteral" as used herein includes, subcutaneous, intravenous, intraarterial, intramuscular, intrasternal, intratendious, intraspinal, intracranial, intrathoracic, infusion techniques or intraperitoneally. The dosage administered will be dependent upon the age, health, and weight of the recipient, kind of concurrent treatment, if any, frequency of treatment, and the nature of the effect desired.

Typical pharmaceutically acceptable carriers include any non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and their derivatives; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate. Coloring agents, releasing agents, coating agents, sweetening, flavoring and perfuming agents, preservatives and antioxidants can also be present in the pharmaceutical composition of the present invention according to the judgment of the formulator.

The composition comprising the active compound according to the present invention may be made up in dosage forms such as granules, powders, tablets, pills, capsules, solutions, suspensions, syrups, elixirs, emulsions, ointments, pastes, creams, lotions, gels, sprays, inhalants or patches. The composition of the present invention may be applied in a variety of solutions. Suitable solutions for use in accordance, with the present invention are sterile, dissolve sufficient amounts of the active compound, and are not harmful for the proposed application. Methods of formulation are within the skill of pharmaceutical formulation chemists and are fully described in such works as Remington's Pharmaceutical Science, 18th Edition, Alfonso R. Gennaro, Ed., Mack Publishing Co., Easton, Pa., USA, 1990.

The term "analogs" refers to a set of compounds which differ from one another only by replacement of one or more heteroatoms, such as O, S, or N, with a different heteroatom.

The term "tautomer forms" refers to structural isomers in rapid equilibrium, such as keto and enol forms of acetylacetone. Tautomer forms are capable of reacting according to either form.

The term "polymorphs" refers to the forms of a polymorphic compound. A polymorphic compound is that which can exist in two or more forms, such as two or more crystalline forms.

The term "derivative" refers to a compound obtained from another compound by a simple chemical process; e.g., acetic acid is a derivative of ethanol by oxidation; N-acetyl ethylamine is a derivative of ethylamine by acetylation.

Pharmaceutically acceptable salts forming part of this invention include base addition salts such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts. Salts may include acid addition salts which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Preferably, the present invention relates to novel dipeptide phenyl ethers of formula (I)

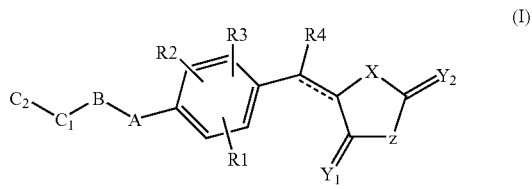

(I)

their derivatives, their analogs, their tautomeric forms, their stereoisomers, their polymorphs, their pharmaceutically acceptable salts, their pharmaceutically acceptable solvates, wherein —— represents an optional double bond; X and Z may be same or different and independently represent oxygen, sulfur or $NR_5$, wherein $R_5$ represents hydrogen or linear or branched alkyl group provided both X and Z are not same when they represent oxygen or sulfur; $Y_1$ and $Y_2$ may be same or different and independently represent oxygen, sulfur or $NR_5$, wherein $R_5$ represents hydrogen or linear or branched alkyl group; $R_1$, $R_2$, $R_3$ and $R_4$ may be same or different and independently represent hydrogen, halogen, hydroxy, nitro, cyano, formyl, mono, di, or unsubstituted amino, alkyl, linear or branched alkoxy group; A represents oxygen, sulfur or NR, wherein R represents hydrogen or linear or branched alkyl; B represents a bond or substituted or unsubstituted aryl; $C_1$ and $C_2$ may be same or different and independently represent amino acid or its derivatives and linked through —NH— of $C_1$ and —CO— of $C_2$, or through —CO— of $C_1$ and —NH— of $C_2$; B is directly linked or linked through alkyl or alkylene groups of 1 to 4 carbon atoms to the α carbon of $C_1$.

Particularly useful compounds and their salts according to the invention include:

5-[4-(4-(2-(2-Amino-3-imidazol-4-ylpropanamido)-2-methoxycarbonylethyl) phenoxy)benzylidene]thiazolidin-2,4-dione 5-[4-(4-(2-(2-Amino-3-imidazol-4-ylpropanamido)-2-carboxyethyl)phenoxy) benzylidene]thiazolidin-2,4-dione 5-[4-(4-(2-(2-Amino-3-imidazol-4-ylpropanamido)-2-carboxyethyl)phenoxy) benzyl]thiazolidin-2,4-dione 5-[4-(4-(2-(2-Amino-3-imidazol-4-ylpropanamido)-2-methoxycarbonylethyl) phenoxy)benzyl]thiazolidin-2,4-dione 3-{4-[4-(2,4-Dioxothiazolidin-5-ylidenemethyl)-phenoxy]-phenyl}-2-[(pyrrolidine-2-carbonyl)-amino]-propionic acid 3-{4-[4-(2,4-Dioxothiazolidin-5-ylidenemethyl)-phenoxy]-phenyl}-2-[(pyrrolidine-2-carbonyl)-amino]-propionic acid methyl ester 3-{4-[4-(2,4-Dioxothiazolidin-5-ylmethyl)-phenoxy]-phenyl}-2-[(pyrrolidine-2-carbonyl)-amino]-propionic acid 3-{4-[4-(2,4-Dioxothiazolidin-5-ylmethyl)-phenoxy]-phenyl}-2-[(pyrrolidine-2-carbonyl)-amino]-propionic acid methyl ester 5-[4-(4-(2-(2-Aminopropanamido)-2-methoxycarbonylethyl)phenoxy)benzyl]thiazolidin-2,4-dione 5-[4-(4-(2-(2-Aminopropanamido)-2-methoxycarbonylethyl) phenoxy) benzylidene]thiazolidin-2,4-dione 5-[4-(4-(2-(2-Aminopropanamido)-2-carboxyethyl)phenoxy)benzyl]thiazolidin-2,4-dione 5-[4-(4-(2-(2-Aminopropanamido)-2-carboxyethyl)phenoxy)benzylidene]thiazolidin-2,4-dione 5-[4-(4-(2-(2-Aminoacetamido)-2-methoxycarbonylethyl) phenoxy)benzylidene]thiazolidin-2,4-dione 5-[4-(4-(2-(2-Aminoacetamido)-2-methoxycarbonylethyl) phenoxy)benzyl]thiazolidin-2,4-dione 5-[4-(4-(2-(2-Aminoacetamido)-2-carboxyethyl)phenoxy) benzylidene]thiazolidin-2,4-dione 5-[4-(4-(2-(2-Aminoacetamido)-2-carboxyethyl)phenoxy) benzyl]thiazolidin-2,4-dione 5-[4-(4-(2-(4-Methylthio-2-aminobutyramido)-2-methoxycarbonylethyl)phenoxy) benzylidene]thiazolidin-2,4-dione 5-[4-(4-(2-(4-Methylthio-2-aminobutyramido)-2-methoxycarbonylethyl) phenoxy)benzyl]thiazolidin-2,4-dione 5-[4-(4-(2-(4-Methylthio-2-aminobutyramido)-2-carboxyethyl)phenoxy) benzylidene]thiazolidin-2,4-dione 5-[4-(4-(2-(4-Methylthio-2-aminobutyramido)-2-carboxyethyl)phenoxy) benzyl]thiazolidin-2,4-dione 5-[4-(4-(2-(2-Amino-3-imidazol-4-ylpropanamido)-2-carboxy ethyl)-2,6-difluorophenoxy)benzylidene]thiazolidin-2,4-dione 5-[4-(4-(2-(2-Amino-3-imidazol-4-ylpropanamido)-2-methoxycarbonylethyl)-2,6-difluorophenoxy)benzylidene]thiazolidin-2,4-dione 5-[4-(4-(2-(2-Amino-3-imidazol-4-ylpropanamido)-2-carboxyethyl)-2,6-difluorophenoxy)benzyl]thiazolidin-2,4-dione 5-[4-(4-(2-(2-Amino-3-imidazol-4-ylpropanamido)-2-methoxycarbonylethyl)-2,6-difluorophenoxy)benzyl]thiazolidin-2,4-dione 5-[4-(4-(2-(2-Amino-3-imidazol-4-ylpropanamido)-2-carboxyethyl)-2,3-difluorophenoxy)benzylidene]thiazolidin-2,4-dione 5-[4-(4-(2-(2-Amino-3-imidazol-4-ylpropanamido)-2methoxycarbonylethyl)-2,3-difluorophenoxy)benzylidene]thiazolidin-2,4-dione 5-[4-(4-(2-(2-Amino-3-imidazol-4-ylpropanamido)-2-carboxyethyl)-2,3-difluorophenoxy)benzyl]thiazolidin-2,4-dione 5-[4-(4-(2-(2-Amino-3-imidazol-4-ylpropanamido)-2-methoxycarbonylethyl)-2,3-difluorophenoxy)benzyl]thiazolidin-2,4-dione 5-[4-(4-(2-(2-Amino-3-imidazol-4-ylpropanamido)-2-carboxyethyl)-2-fluorophenoxy)benzylidene]thiazolidin-2,4-dione 5-[4-(4-(2-(2-Amino-3-imidazol-4-ylpropanamido)-2-methoxycarbonylethyl)-2-fluorophenoxy)benzylidene]thiazolidin-2,4-dione 5-[4-(4-(2-(2-Amino-3-imidazol-4-ylpropanamido)-2-carboxyethyl)-2-fluorophenoxy)benzyl]thiazolidin-2,4-dione 5-[4-(4-(2-(2-Amino-3-imidazol-4-ylpropanamido)-2-methoxycarbonylethyl)-2-fluorophenoxy)benzyl]thiazolidin-2,4-dione 33. 5-[4-(4-(2-(2-Amino-3-imidazol-4-ylpropanamido)-2-carboxyethyl)-3-fluorophenoxy)benzylidene]thiazolidin-2,4-dione 5-[4-(4-(2-(2-Amino-3-imidazol-4-ylpropanamido)-2-methoxycarbonylethyl)-3-fluorophenoxy)benzylidene]thiazolidin-2,4-dione 5-[4-(4-(2-(2-Amino-3-imidazol-4-ylpropanamido)-2-carboxyethyl)-3-fluorophenoxy)benzyl]thiazolidin-2,4-dione 5-[4-(4-(2-(2-Amino-3-imidazol-4-ylpropanamido)-2-methoxycarbonylethyl)-3-fluorophenoxy)benzyl]thiazolidin-2,4-dione 3-{4-[4-(2,4-Dioxo-thiazolidin-5-ylidenemethyl)-3,5-difluoro-phenoxy]-phenyl}-2-[(pyrrolidine-2-carbonyl)-amino]-propionic acid 3-{4-[4-(2,4-Dioxo-thiazolidin-5-ylidenemethyl)-3,5-difluoro-phenoxy]-phenyl}-2-[(pyrrolidine-2-carbonyl)-amino]-propionic acid methyl ester 3-{4-[4-(2,4-Dioxo-thiazolidin-5-ylmethyl)-3,5-difluoro-phenoxy]-phenyl}-2-[(pyrrolidine-2-carbonyl)-amino]-propionic acid 3-{4-[4-(2,4-Dioxo-thiazolidin-5-ylmethyl)-3,5-difluoro-phenoxy]-phenyl}-2-[(pyrrolidine-2-carbonyl)-amino]-propionic acid methyl ester 3-{4-[4-(2,4-Dioxo-thiazolidin-5-ylidenemethyl)-2,3-difluoro-phenoxy]-phenyl}-2-[(pyrrolidine-2-carbonyl)-amino]-propionic acid 3-{4-[4-(2,4-Dioxo-thiazolidin-5-ylidenemethyl)-2,3-difluoro-phenoxy]-phenyl}-2-[(pyrrolidine-2-carbonyl)-amino]-propionic acid methyl ester 3-{(4-[4-(2,4-Dioxo-thiazolidin-5-ylmethyl)-2,3-difluoro-phenoxy]-phenyl}-2-[(pyrrolidine-2-carbonyl)-amino]-propionic acid 3-{(4-[4-(2,4-Dioxo-thiazolidin-5-ylmethyl)-2,3-difluoro-phenoxy]-phenyl}-2-[(pyrrolidine-2-carbonyl)-amino]-propionic acid methyl ester 3-{4-[4-(2,4-Dioxo-thiazolidin-5-ylidenemethyl)-3-fluoro-phenoxy]-phenyl}-2-[(pyrrolidine-2-carbonyl)-amino]-propionic acid 3-{4-[4-(2,4-Dioxo-thiazolidin-5-ylidenemethyl)-3-fluoro-phenoxy]-phenyl}-2-[(pyrrolidine-2-carbonyl)-amino]-propionic acid methyl ester 3-{4-[4-(2,4-Dioxo-thiazolidin-5-ylmethyl)-3-fluoro-phenoxy]-phenyl}-2-[(pyrrolidine-2-carbonyl)-amino]-propionic acid 3-{4-[4-(2,4-Dioxo-thiazolidin-5-ylmethyl)-3-fluoro-phenoxy]-phenyl}-2-[(pyrrolidine-2-carbonyl)-amino]-propionic acid methyl ester 3-{4-[4-(2,4-Dioxo-thiazolidin-5-ylidenemethyl)-2-fluoro-phenoxy]-phenyl}-2-[(pyrrolidine-2-carbonyl)-amino]-propionic acid 3-{4-[4-(2,4-Dioxo-thiazolidin-5-ylidenemethyl)-2-fluoro-phenoxy]-phenyl}-2-[(pyrrolidine-2-carbonyl)-amino]-propionic acid methyl ester 3-{4-[4-(2,4-Dioxo-thiazolidin-5-ylmethyl)-2-fluoro-phenoxy]-phenyl}-2-[(pyrrolidine-2-carbonyl)-amino]-propionic acid 3-{4-[4-(2,4-Dioxo-thiazolidin-5-ylmethyl)-2-fluoro-phenoxy]-phenyl}-2-[(pyrrolidine-2-carbonyl)-amino]-propionic acid methyl ester 2-(2-Amino-3-{4-[4-(2,4-dioxothiazolidin-5-ylmethyl)-phenoxy]-phenyl}-propionylamino)-3-(3H-imidazol-4-yl)-propionic acid 1-(2-Amino-3-{4-[4-(2,4-dioxothiazolidin-5-ylmethyl)-2-fluorophenoxy]-phenyl}-propionyl)-pyrrolidine-2-carboxylic acid 2-(2-Amino-3-{4-[4-(2,4-dioxothiazolidin-5-ylmethyl)-phenoxy]-phenyl}-propionylamino)-propionic acid 1-(2-Amino-3-{4-[4-(2,4-dioxothiazolidin-5-ylmethyl)-phenoxy]-phenyl}-propionylamino)-acetic acid 2-(2-Amino-3-{4-[4-(2,4-dioxothiazolidin-5-ylmethyl)-phenoxy]-phenyl}-propionylamino)-4-methylsulfanylbutyric acid 5-Amino-6-{4-[4-(2,4-dioxothiazolidin-5-ylmethyl)-phenoxy]-phenyl}-2-(1H-indol-3-ylmethyl)-4-oxohexanoic acid 2-(2-Amino-3-{4-[4-(2,4-dioxothiazolidin-5-ylmethyl)-phenoxy]-phenyl}-propionylamino)-4-carbamoylbutyric acid 2-(2-Amino-3-{4-[4-(2,4-dioxothiazolidin-5-ylmethyl)-phenoxy]-phenyl}-propionylamino)-3-phenylpropionic acid 2-(2-Amino-3-{4-[4-(2,4-dioxothiazolidin-5-ylmethyl)-phenoxy]-phenyl}-propionylamino)-5-guanidinopentanoic acid 2-(2-Amino-3-{4-[4-(2,4-dioxothiazolidin-5-ylmethyl)-phenoxy]-phenyl}-propionylamino)-3-mercaptopropionic acid.

Compounds within the scope of the invention include those in the table below:

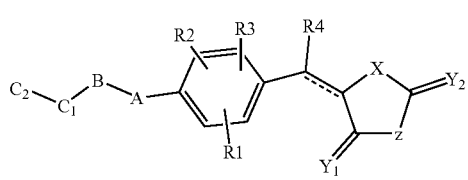
(I)
| C₂ | C₁ | B | A | R₁, R₂, R₃ | R₄ | — | X | Z | Y₁, Y₂ |
|---|---|---|---|---|---|---|---|---|---|
| 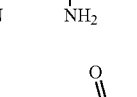 | 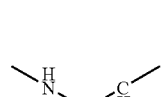 | 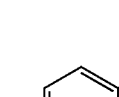 | O | H, H, H | H | bond | S | NH | O, O |
| 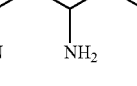 | 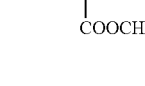 | 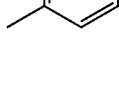 | O | H, H, H | H | bond | S | NH | O, O |
| 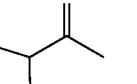 | 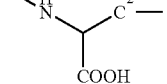 | 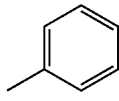 | O | H, H, H | H | bond | S | NH | O, O |
| 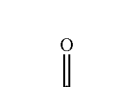 | 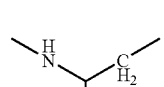 | 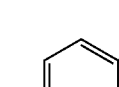 | O | H, H, H | H | bond | S | NH | O, O |
|  | 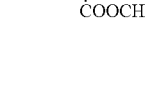 | 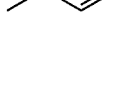 | O | H, H, H | H | bond | S | NH | O, O |
| 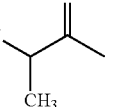 | 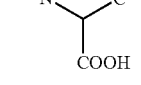 | 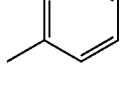 | O | H, H, H | H | bond | S | NH | O, O |
| 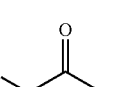 | 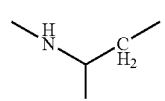 | 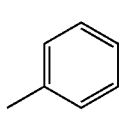 | O | H, H, H | H | bond | S | NH | O, O |
| 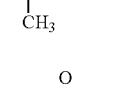 |  |  | O | H, H, H | H | bond | S | NH | O, O |
| 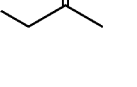 | 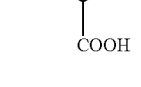 | 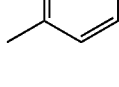 | O | H, H, H | H | bond | S | NH | O, O |

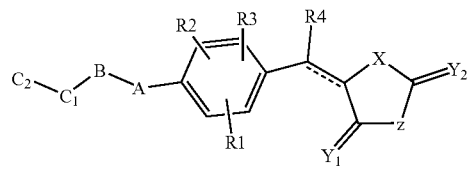

| C₂ | C₁ | B | A | R₁, R₂, R₃ | R₄ | — | X | Z | Y1, Y2 |
|---|---|---|---|---|---|---|---|---|---|
| H₃C-S-CH₂CH₂-CH(NH₂)-C(O)- | -NH-CH(COOCH₃)-CH₂- | phenyl | O | H, H, H | H | bond | S | NH | O, O |
| H₂N-(CH₂)₄-CH(NH₂)-C(O)- | -NH-CH(COOH)-CH₂- | phenyl | O | H, H, H | H | bond | S | NH | O, O |
| H₂N-(CH₂)₄-CH(NH₂)-C(O)- | -NH-CH(COOCH₃)-CH₂- | phenyl | O | H, H, H | H | bond | S | NH | O, O |
| HS-CH₂-CH(NH₂)-C(O)- | -NH-CH(COOH)-CH₂- | phenyl | O | H, H, H | H | bond | S | NH | O, O |
| HS-CH₂-CH(NH₂)-C(O)- | -NH-CH(COOCH₃)-CH₂- | phenyl | O | H, H, H | H | bond | S | NH | O, O |
| H₂N-C(O)-CH₂CH₂-CH(NH₂)-C(O)- | -NH-CH(COOH)-CH₂- | phenyl | O | H, H, H | H | bond | S | NH | O, O |
| H₂N-C(O)-CH₂CH₂-CH(NH₂)-C(O)- | -NH-CH(COOCH₃)-CH₂- | phenyl | O | H, H, H | H | bond | S | NH | O, O |
| CH₃CH₂-CH(CH₃)-CH(NH₂)-C(O)- | -NH-CH(COOH)-CH₂- | phenyl | O | H, H, H | H | bond | S | NH | O, O |
| CH₃CH₂-CH(CH₃)-CH(NH₂)-C(O)- | -NH-CH(COOCH₃)-CH₂- | phenyl | O | H, H, H | H | bond | S | NH | O, O |

-continued
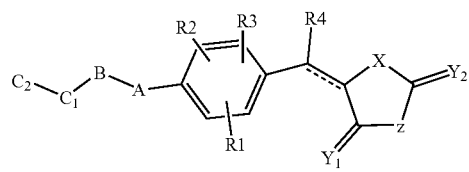
(I)
| C₂ | C₁ | B | A | R₁, R₂, R₃ | R₄ | — | X | Z | Y1, Y2 |
|---|---|---|---|---|---|---|---|---|---|
| | | | O | H, H, H | H | bond | S | NH | O, O |
| | | | O | H, H, H | H | bond | S | NH | O, O |
| | | | O | H, H, H | H | bond | S | NH | O, O |
| | | | O | H, H, H | H | bond | S | NH | O, O |
| | | | O | H, H, H | H | bond | S | NH | O, O |
| | | | O | H, H, H | H | bond | S | NH | O, O |
| | | | O | H, H, H | H | bond | S | NH | O, O |
| | | | O | H, H, H | H | bond | S | NH | O, O |
| | | | O | H, H, H | H | bond | S | NH | O, O |

-continued
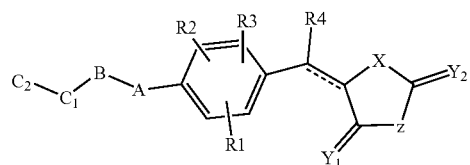
(I)
| C₂ | C₁ | B | A | R₁, R₂, R₃ | R₄ | — | X | Z | Y1, Y2 |
|---|---|---|---|---|---|---|---|---|---|
|  |  |  | O | H, H, H | H | bond | S | NH | O, O |
| 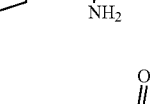 | 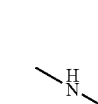 | 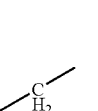 | O | H, H, H | H | bond | S | NH | O, O |
| 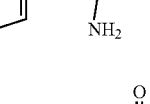 | 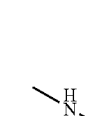 | 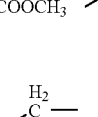 | O | H, H, H | H | bond | S | NH | O, O |
| 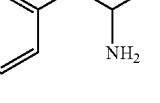 | 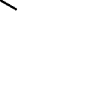 | 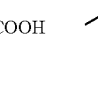 | O | H, H, H | H | bond | S | NH | O, O |
| 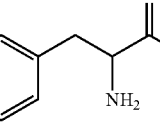 | 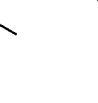 | 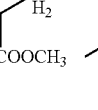 | O | H, H, H | H | bond | S | NH | O, O |
| 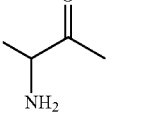 | 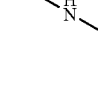 | bond | O | H, 2-F, 6-F | H | bond | S | NH | O, O |
| 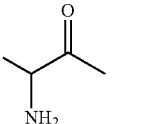 | 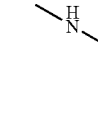 | bond | O | H, 2-F, 6-F | H | bond | S | NH | O, O |
| 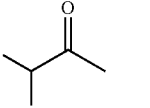 | 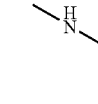 | bond | O | H, 3-F, 6-F | H | bond | S | NH | O, O |
|  |  | bond | O | H, 3-F, 6-F | H | bond | S | NH | O, O |

-continued
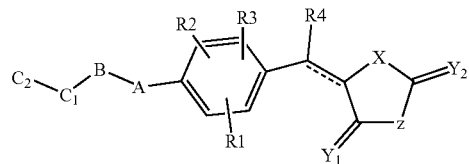
(I)
| C₂ | C₁ | B | A | R₁, R₂, R₃ | R₄ | — | X | Z | Y1, Y2 |
|---|---|---|---|---|---|---|---|---|---|
| 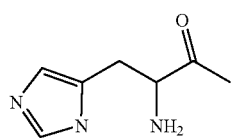 | 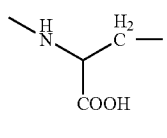 | 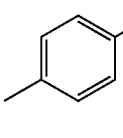 | O | H, H, H | H | No bond | S | NH | O, O |
| 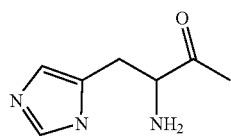 | 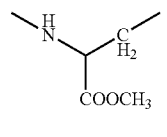 | 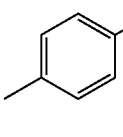 | O | H, H, H | H | No bond | S | NH | O, O |
| 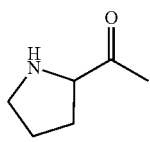 | 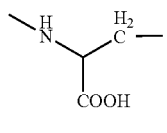 | 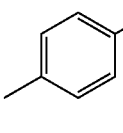 | O | H, H, H | H | No bond | S | NH | O, O |
| 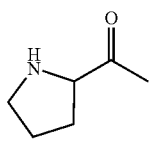 | 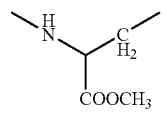 | 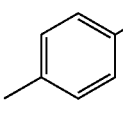 | O | H, H, H | H | No bond | S | NH | O, O |
| 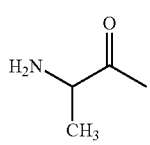 | 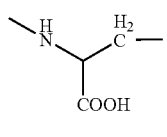 | 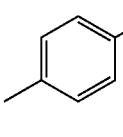 | O | H, H, H | H | No bond | S | NH | O, O |
| 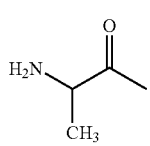 | 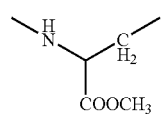 | 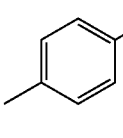 | O | H, H, H | H | No bond | S | NH | O, O |
| 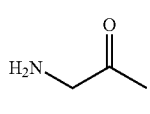 | 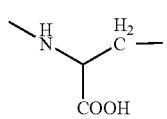 | 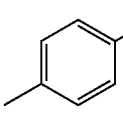 | O | H, H, H | H | No bond | S | NH | O, O |
| 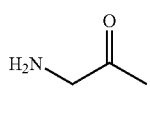 | 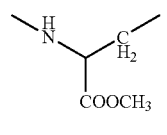 | 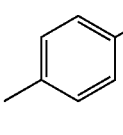 | O | H, H, H | H | No bond | S | NH | O, O |
| 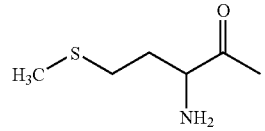 | 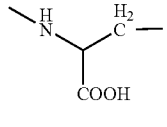 | 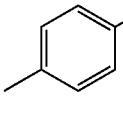 | O | H, H, H | H | No bond | S | NH | O, O |

-continued

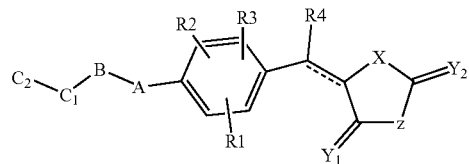

(I)

| C₂ | C₁ | B | A | R₁, R₂, R₃ | R₄ | — | X | Z | Y1, Y2 |
|---|---|---|---|---|---|---|---|---|---|
| H₃C-S-CH₂CH₂-CH(NH₂)-C(O)- | -NH-CH(COOCH₃)-CH₂- | -C₆H₄- | O | H, H, H | H | No bond | S | NH | O, O |
| (imidazole)-CH₂-CH(NH₂)-C(O)- | -NH-CH(COOH)-CH₂- | -C₆H₄- | O | H, 2-F, 6-F | H | bond | S | NH | O, O |
| (imidazole)-CH₂-CH(NH₂)-C(O)- | -NH-CH(COOCH₃)-CH₂- | -C₆H₄- | O | H, 2-F, 6-F | H | bond | S | NH | O, O |
| (pyrrolidine)-C(O)- | -NH-CH(COOH)-CH₂- | -C₆H₄- | O | H, 2-F, 6-F | H | bond | S | NH | O, O |
| (pyrrolidine)-C(O)- | -NH-CH(COOCH₃)-CH₂- | -C₆H₄- | O | H, 2-F, 6-F | H | bond | S | NH | O, O |
| H₂N-CH(CH₃)-C(O)- | -NH-CH(COOH)-CH₂- | -C₆H₄- | O | H, 2-F, 6-F | H | bond | S | NH | O, O |
| H₂N-CH(CH₃)-C(O)- | -NH-CH(COOCH₃)-CH₂- | -C₆H₄- | O | H, 2-F, 6-F | H | bond | S | NH | O, O |
| H₂N-CH₂-C(O)- | -NH-CH(COOH)-CH₂- | -C₆H₄- | O | H, 2-F, 6-F | | bond | S | NH | O, O |
| H₂N-CH₂-C(O)- | -NH-CH(COOCH₃)-CH₂- | -C₆H₄- | O | H, 2-F, 6-F | | bond | S | NH | O, O |

-continued

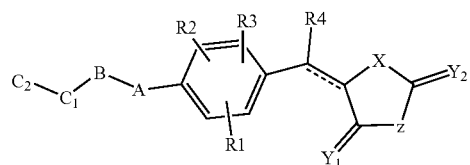
(I)

| C₂ | C₁ | B | A | R₁, R₂, R₃ | R₄ | — | X | Z | Y1, Y2 |
|---|---|---|---|---|---|---|---|---|---|
| H₃C-S-...-NH₂ (methionine-like ketone) | NH-CH(COOH)-CH₂- | p-phenylene | O | H, 2-F, 6-F |  | bond | S | NH | O, O |
| H₃C-S-...-NH₂ | NH-CH(COOCH₃)-CH₂- | p-phenylene | O | H, 2-F, 6-F |  | bond | S | NH | O, O |
| imidazolyl-CH₂-CH(NH₂)-C(O)- | NH-CH(COOH)-CH₂- | p-phenylene | O | H, 3-F, 6-F | H | bond | S | NH | O, O |
|  | NH-CH(COOCH₃)-CH₂- | p-phenylene | O | H, 3-F, 6-F | H | bond | S | NH | O, O |
| pyrrolidinyl-C(O)- | NH-CH(COOH)-CH₂- | p-phenylene | O | H, 3-F, 6-F | H | bond | S | NH | O, O |
|  | NH-CH(COOCH₃)-CH₂- | p-phenylene | O | H, 3-F, 6-F | H | bond | S | NH | O, O |
| H₂N-CH(CH₃)-C(O)- | NH-CH(COOH)-CH₂- | p-phenylene | O | H, 3-F, 6-F | H | bond | S | NH | O, O |
|  | NH-CH(COOCH₃)-CH₂- | p-phenylene | O | H, 3-F, 6-F | H | bond | S | NH | O, O |
| H₂N-CH₂-C(O)- | NH-CH(COOH)-CH₂- | p-phenylene | O | H, 3-F, 6-F | H | bond | S | NH | O, O |
|  | NH-CH(COOCH₃)-CH₂- | p-phenylene | O | H, 3-F, 6-F | H | bond | S | NH | O, O |

-continued

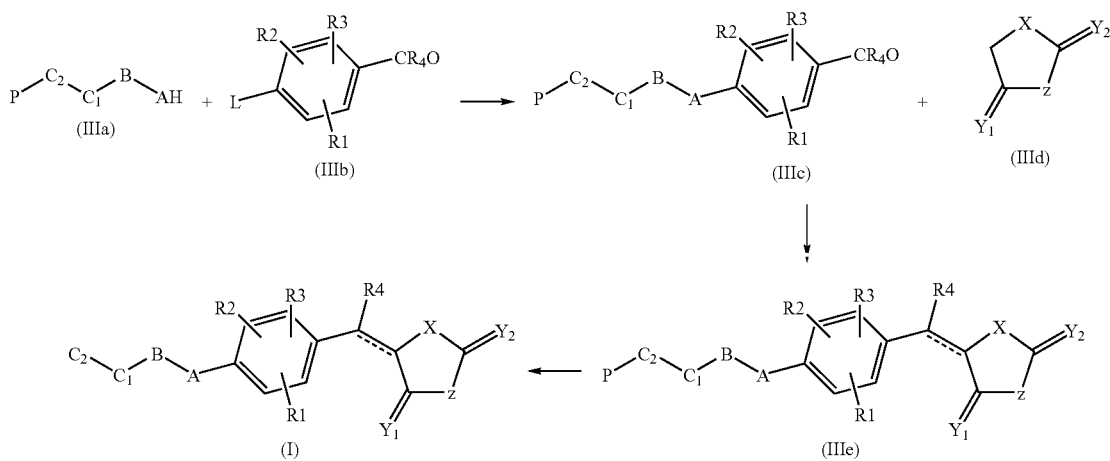

Preferred salts for the list of compounds above are the hydrochloride, hydrobromide, sodium, potassium or magnesium salts.

According to another feature of the present invention, there is provided a process for the preparation of novel dipeptide phenyl ethers of formula (I), wherein — represents a bond or no bond and all other symbols are as defined earlier, as shown in scheme-I reaction may be carried out in an inert atmosphere which may be maintained by using inert gases such as $N_2$, Ar or He. The reaction may be effected in the presence of a base such as $K_2CO_3$, $Na_2CO_3$, NaH or mixtures thereof. The reaction temperature may range from 20° C. to 150° C., preferably at a temperature in the range of 30° C. to 100° C. The duration of the reaction may range from 1 to 72 hours, preferably from 6 to 24 hours.

The reaction of compound of formula (IIIa) wherein P represents an amino or carboxy protecting group depending upon the end group on $C_2$, and all other symbols are as defined earlier with the compound of formula (IIIb) wherein L represents a leaving group, and all other symbols are as defined earlier to produce a compound of formula (IIIc) may be carried out in the presence of solvents such as THF, DMF, DMSO, DME and the like or mixtures of solvents may be used. Side chain function protecting groups are also present on $C_2$ or $C_1$, as needed, but are not shown in Scheme I. The The conventional protecting groups used are those that can be easily removed and are selected from t-Boc, CBz, F-moc, etc.

The reaction of the compound of the general formula (IIIc) with compound of formula (IIId) to yield a compound of formula (IIIe) may be carried out neat in the presence of sodium acetate or in the presence of a solvent such as benzene, toluene, methoxyethanol or mixtures thereof. The reaction temperature may range from 80° C. to 180° C., when the reaction is carried out neat in the presence of sodium acetate.

Suitable catalyst such as piperidinium acetate or benzoate, sodium acetate or mixtures of catalysts may also be employed. Sodium acetate can be used in the presence of solvent, but it is preferred that sodium acetate is used neat. The water produced in the reaction may be removed, for example, by using Dean Stark water separator or by using water absorbing agents like molecular sieves.

The deprotection of amino acid group of formula (IIIe) to yield compound of formula (I) may be carried out using acids such as HCl, sulfuric acid, acetic acid in the presence of solvents such as DCM, ethyl acetate, water and the like or mixture thereof at a temperature in the range of –10° C. to 50° C.

According to another feature of the present invention, there is provided a process for the preparation of novel dipeptide phenyl ethers of formula (I), wherein — represents a bond or no bond and all other symbols are as defined earlier, as shown in scheme- II

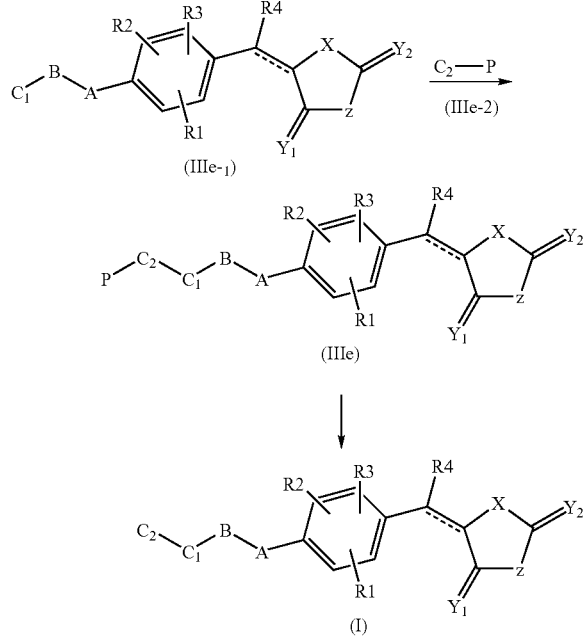

The reaction of compound of formula (IIIe-1) wherein all symbols are as defined earlier with the compound of formula (IIIe-2) where $C_2$ is as defined above and P represents a protecting group to produce a compound of formula (IIIe) may be carried out in the presence of solvents such as THF, DMF, DMSO, DME and the like or mixtures of solvents may be used. A protecting group (not shown) may also be required on $C_1$, particularly if $C_2$ is to be linked to the C-terminus of $C_1$. The reaction may be carried out in the presence of coupling agents such as dicyclohexylcarbodiimide, hydroxy benzotriazole, carbonyldiimidazole and the like. The reaction may be carried out in an inert atmosphere which may be maintained by using inert gases such as $N_2$, Ar or He. The reaction may be effected in the presence of a base such as $K_2CO_3$, $Na_2CO_3$, NaH or mixtures thereof. The reaction temperature may range from 20° C. to 150° C., preferably at a temperature in the range of 30° C. to 100° C. The duration of the reaction may range from 1 to 72 hours, preferably from 6 to 24 hours.

The conventional protecting groups used are those that can be easily removed and are selected from t-Boc, CBz, F-moc, etc.

The deprotection of amino acid group of formula (IIIe) to yield compound of formula (I) may be carried out using acids such as HCl, sulfuric acid, acetic acid in the presence of solvents such as DCM, ethyl acetate, water and the like or mixture thereof at a temperature in the range of –10° C. to 50° C.

In another embodiment of the present invention, there is provided a process for the preparation of novel dipeptide phenyl ethers of formula (I), wherein — represents no bond by reducing compounds of formula (I) wherein — represents a bond and all other symbols are as defined earlier. The selective reduction may be carried out in the presence of gaseous hydrogen and a catalyst such as Pd/C, Rh/C, Pt/C, Raney Nickel, and the like. Mixtures of catalysts may be used. The reaction may be conducted in the presence of solvents such as methanol, ethanol, dioxane, acetic acid, ethyl acetate and the like. Mixtures of solvents may be used. A pressure between atmospheric pressure to 100 psi may be employed. The catalyst may be 5-10% Pd/C and the amount of catalyst used may range from 50-300% w/w. The reaction may also be carried out by employing metal solvent reduction such as magnesium in methanol or sodium amalgam in methanol. The reaction may also be carried out with alkali metal borohydrides such as $LiBH_4$, $NaBH_4$, $KBH_4$ and the like in the presence of cobalt salt such as $CoCl_2$ and ligands, preferably bidentated ligands such as 2,2'-bipyridyl, 1,10-phenanthroline, bisoximes and the like.

In another embodiment of the present invention, the compounds of general formula (I) wherein Z represents sulfur, — represents no bond can be prepared by reacting the compound of formula (IIIf)

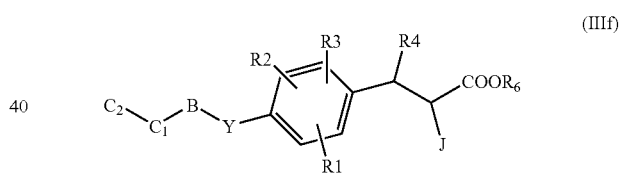

wherein J is halogen atom like chlorine, bromine or iodine and $R_6$ is a lower alkyl group and all other symbols are as defined earlier with thiourea followed by treatment with an acid.

The reaction of compound of general formula (IIIf) with thiourea is carried out in the presence of alcoholic solvent such as methanol, ethanol, propanol, isobutanol, 2-methoxybutanol, etc or DMSO or sulfolane. The reaction may be conducted at a temperature in the range between 20° C. and the reflux temperature of the solvent used. Bases such as NaOAc, KOAc, NaOMe, NaOEt etc. can be used.

In yet another embodiment of the present invention, the compounds of the general formula (I) wherein — represents a bond and all other symbols are as defined earlier can also be prepared by reacting a compound of formula (IIIg)

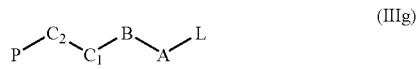

wherein L is a leaving group such as halogen atom like chlorine, bromine or iodine; or methanesulfonate, trifluoromethanesulfonate, p-toluenesulfonate and the like and P represents protecting group all other symbols are as defined earlier, with a compound of the formula (IIIh).

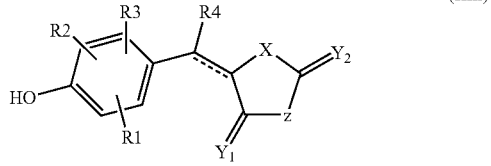
(IIIh)

wherein all symbols are as defined earlier.

The reaction of compound of general formula (IIIg) with a compound of general formula (IIIh) to produce a compound of general formula (I) may be carried out in the presence of solvents such as THF, DMF, DMSO, DME and the like or mixtures thereof. The reaction may be carried out in an inert atmosphere which may be maintained by using inert gases such as $N_2$, Ar or He. The reaction may be effected in the presence of a base such as alkalis like sodium hydroxide or potassium hydroxide; alkali metal carbonates like sodium carbonate or potassium carbonate; alkali metal hydrides such as sodium hydride; organometallic bases like n-butyl lithium; alkali metal amides like sodamide, or mixtures thereof. Multiple solvents and bases can be used. The amount of base may range from 1 to 5 equivalents, preferably 1 to 3 equivalents. The reaction temperature may be in the range of 0 °C. to 120° C., preferably at a temperature in the range of 20° C. to 100° C. The duration of the reaction may range from 0.5 to 24 hours, preferably from 0.5 to 6 hrs.

In yet another embodiment of the present invention, the compounds of the general formula (I) wherein — represents a bond and all other symbols are as defined earlier can also be prepared by reacting a compound of formula (IIIi)

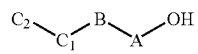
(IIIi)

wherein all symbols are as defined earlier with a compound of the formula (IIIh).

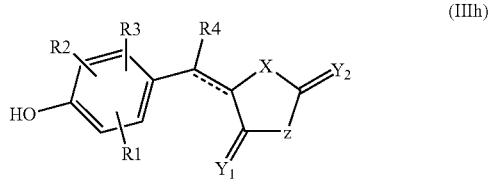
(IIIh)

wherein all symbols are as defined earlier.

The reaction of compound of general formula (IIIi) with a compound of general formula (IIIh) to produce a compound of general formula (I) may be carried out in the presence of solvents such as THF, DMF, DMSO, DME and the like or mixtures thereof. The reaction may be carried out in an inert atmosphere which may be maintained by using inert gases such as $N_2$, Ar or He. The reaction may be effected in the presence of a base such as alkalis like sodium hydroxide or potassium hydroxide; alkali metal carbonates like sodium carbonate or potassium carbonate; alkali metal hydrides such as sodium hydride; organometallic bases like n-butyl lithium; alkali metal amides like sodamide, or mixtures thereof. Multiple solvents and bases can be used. The amount of base may range from 1 to 5 equivalents, preferably 1 to 3 equivalents. The reaction temperature may be in the range of 0° C. to 120° C., preferably at a temperature in the range of 20° C. to 100° C. The duration of the reaction may range from 0.5 to 24 hours, preferably from 0.5 to 6 hrs.

In yet another embodiment of the present invention, there is provided an intermediate of formula (IIIc)

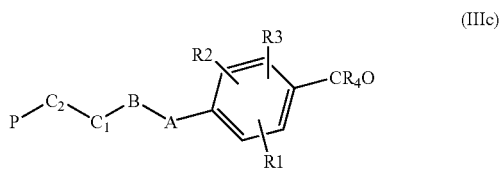
(IIIc)

their derivatives, their analogs, their tautomeric forms, their stereoisomers, their polymorphs, their pharmaceutically acceptable salts, their pharmaceutically acceptable solvates, wherein $R_1$, $R_2$ and $R_3$ may be same or different and independently represent hydrogen, halogen, hydroxy, nitro, cyano, formyl, mono-, di-, or unsubstituted amino, linear or branched ($C_1$-$C_6$) alkyl, linear or branched ($C_1$-$C_6$) alkoxy group; $R_4$ represents hydrogen; A represents oxygen, sulfur or NR, wherein R represents hydrogen or linear or branched ($C_1$-$C_6$) alkyl; B represents a bond or substituted or unsubstituted aryl, heterocyclyl or heteroaryl ring of 5 to 14 carbon and hetero atoms; $C_1$ and $C_2$ may be same or different and independently represent amino acid or its derivatives and linked through —NH— of $C_1$ and —CO— of $C_2$ or through —CO— of $C_1$ and —NH— of $C_2$; B is directly linked or linked through alkyl or alkylene groups of 1 to 4 carbon atoms to the a carbon of $C_1$; P is a protecting group.

In yet another embodiment of the present invention, there is provided an intermediate of formula (IIIe)

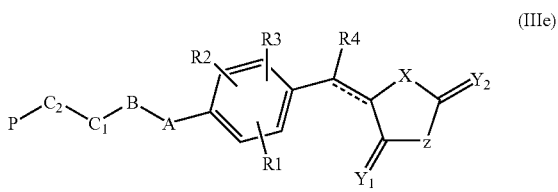
(IIIe)

their derivatives, their analogs, their tautomeric forms, their stereoisomers, their polymorphs, their pharmaceutically acceptable salts, their pharmaceutically acceptable solvates, wherein —— represents optional double bond; X and Z may be same or different and independently represent oxygen, sulfur or $NR_5$, wherein $R_5$ represents hydrogen or linear or branched ($C_1$-$C_6$) alkyl group provided both X and Z are not same when they represent oxygen or sulfur; $Y_1$ and $Y_2$ may be same or different and independently represent oxygen, sulfur or $NR_5$; $R_1$, $R_2$, $R_3$ $R_4$, A, B, $C_1$, $C_2$ and P are as described above.

In yet another embodiment of the present invention, there is provided an intermediate of formula (IIIf)

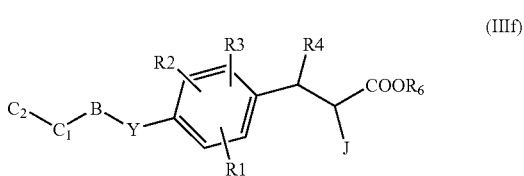

their derivatives, their analogs, their tautomeric forms, their stereoisomers, their polymorphs, their pharmaceutically acceptable salts, their pharmaceutically acceptable solvates, wherein —— represents optional double bond; $R_1, R_2, R_3, R_4$, A, B, $C_1, C_2$, are as described above; J represents halogen atom and $R_6$ represents linear or branched ($C_1$-$C_6$) alkyl group.

It is appreciated that in any of the above-mentioned reactions, any reactive group in the substrate molecule may be protected according to conventional chemical practice. Suitable protecting groups in any of the above-mentioned reactions are those used conventionally in the art. The methods of formation and removal of such protecting groups are those conventional methods appropriate to the molecule being protected.

The invention is explained in detail in the examples given below which are provided by way of illustration only and therefore should not be construed to limit the scope of the invention.

DIPEPTIDE PHENYL ETHERS

EXAMPLE 1

Preparation of 5-[4-(4-(2-(2-amino-3-imidazol-4-ylpropanamido)-2-methoxy carbonylethyl)phenoxy)benzyl]thiazolidin-2,4-dione dihydrochloride. (Compound A)

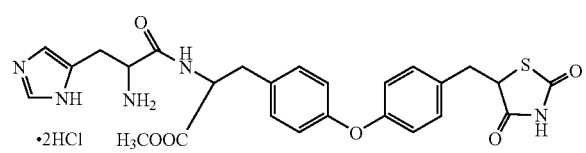

Method 1

Step (i)

5-[4-(4-(2-(2-N-t-Butoxycarbonylamino-3-imidazol-4-yl-propanamido)-2-methoxy carbonylethyl)phenoxy)benzylidene]thiazolidin-2,4-dione Method A Diethylamine (1.04 ml, 6.0 mmol) and N,N'-dicyclohexylcarbodiimide (0.64 g, 3.13 mmol) were added to the stirred suspension of 5-[4-(4-(2-amino-2-methoxycarbonylethyl) phenoxy)benzylidene]thiazolidin-2,4-dione hydrochloride (1.3 g, 3.0 mmol), 2-N-t-butoxy-carbonylamino-4-imidazole propionic acid (0.8 g, 3.13 mmol) and hydroxyl benzotriazole (0.42 g, 3.13 mmol) in N,N-dimethyl formamide (15 ml). The stirring was continued for 24 h and the reaction mixture was concentrated in vacuum. The obtained residue was washed with 10% sodium bicarbonate, brine and purified with preparative HPLC to yield the title compound (1.5 g, yield 79%).

Method B

A solution of 5-[4-(4-(2-amino-2-methoxycarbonylethyl) phenoxy)benzylidene]thiazolidin-2,4-dione hydrochloride (6 g, 13.7 mmol) and 2-N-t-butoxy-carbonylamino-4-imidazole propionic acid (5.2 g, 20.3 mmol) in N,N-dimethylformamide (200 ml) was stirred for 1 h at −10° C. N,N'-Dicyclohexylcarbodiimide (4.5 g, 21.8 mmol) was added to this solution and stirring was continued for 12 h at ambient temperature. Water (1800 ml) was added to the reaction mixture, stirred for 20 minutes and extracted with ethyl acetate (3×400 ml). Ethyl acetate extract was washed with water (300 ml), dried over anhydrous sodium sulfate and concentrated to furnish the title compound, which was purified by column chromatography (3.4 g, yield 51%).

$^1$HNMR (DMSO-$d_6$, 400 MHz): δ 1.3 (s, 9H), 2.6 (m, 2H), 2.8 (m, 1H), 3.0 (m, 1H), 3.6 (d, 3H), 4.1 (m, 1H), 4.5 (d, 1H), 6.7 (s, 1H), 6.8 (dd, 1H), 7.0 (m, 4H), 7.2 (d, 2H), 7.5 (d, 2H), 7.6 (d, 2H), 8.2 (dd, 1H); m/z$^{M+1}$ 636.2.

Step (ii)

5-[4-(4-(2-(2-Amino-3-imidazol-4-ylpropanamido)-2-methoxycarbonylethyl)phenoxy)benzylidene]thiazolidin-2,4-dione dihydrochloride (Compound B)

HCl gas was bubbled to a solution of 5-[4-(4-(2-(2-N-t-butoxycarbonylamino-3-imidazol-4-ylpropanamido)-2-methoxycarbonylethyl)phenoxy)benzylidine]thiazolidin-2,4-dione (3.4 g, 5.3 mmol) in acetic acid (60 ml) at ambient temperature for 1 h. The stirring was continued for 1 h, acetic acid was removed under high vacuum and the residue was triturated with ethyl ether (2×10 ml) to yield the title compound as yellow solid (2.8 g, yield 87.5%).

$^1$HNMR (DMSO-$d_6$, 400 MHz): δ 2.9 (m, 4H), 3.5 (d, 3H), 4.2 (d, 1H), 4.5 (m, 1H), 5.7 (s, 1H), 7.0 (m, 4H), 7.2 (m, 2H), 7.4 (s, 1H), 7.5 (m, 2H), 7.8 (s, 1H), 8.5 (bs, 3H), 9.0 (s, 1H), 9.3 (t, 1H); m/z$^{M+1}$ 536.2.

Step (iii)

5-[4-(4-(2-(2-Amino-3-imidazol-4-ylpropanamido)-2-methoxycarbonylethyl)phenoxy)benzyl]thiazolidin-2,4-dione dihydrochloride A mixture of 5-[4-(4-(2-(2-amino-3-imidazol-4-ylpropanamido)-2-methoxycarbonyl ethyl)phenoxy)benzylidine] thiazolidin-2,4-dione dihydrochloride (0.5 g, 0.82 mmol) in methanol (15 ml) and Pd/C (5%, 0.15 g) was hydrogenated at 60 psi over night. The catalyst was filtered off and filtrate was evaporated under vacuum to afford the title compound (0.48 g, yield 96%).

Method: 2

Preparation of 5-[4-(4-(2-(2-amino-3-imidazol-4-ylpropanamido)-2-methoxy carbonylethyl)phenoxy)benzyl]thiazolidin-2,4-dione dihydrochloride

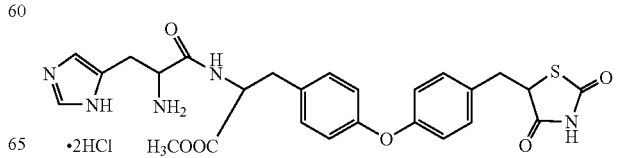

Step (i)

5-[4-(4-(2-(2-N-t-Butoxycarbonylamino-3-imidazol-4-yl-propanamido-2-methoxy carbonylethyl)phenoxy)benzyl]thiazolidin-2,4-dione A solution of 5-[4-(4-(2-amino-2-methoxycarbonylethyl) phenoxy)benzyl]thiazolidin-2,4-dione hydrochloride (4 g, 9.16 mmol) and 2-N-t-butoxycarbonylamino-4-imidazole propionic acid (3.2 g, 12.82 mmol) in N,N-dimethylformamide (50 ml) was stirred for 1 h at –10° C. N,N'-Dicyclohexylcarbodiimide (3.01 g, 14.65 mmol) was added to this solution and stirred for 10 h at ambient temperature. Water (600 ml) was added to the reaction mixture, stirred for 20 minutes and extracted with ethyl acetate (3×300 ml). Ethyl acetate extract was washed with water (100 ml), dried over anhydrous sodium sulfate and concentrated to give the title compound, (5 g, yield 86%).

$^1$HNMR (CD$_3$OD-d$_4$, 400 MHz): δ 1.4 (s, 9H), 2.7 (m, 3H), 3.1 (d, 2H), 3.4 (d, 1H), 3.7 (d, 3H), 4.3 (s, 1H), 4.7 (m, 2H), 4.9 (s, 1H), 6.9 (m, 5H), 7.2 (m, 4H), 7.5 (d, 1H), 7.6 (s, 1H), 7.7 (d, 1H), 7.9 (s, 1H); m/z$^{M+1}$ 638.

Step (ii)

5-[4-(4-(2-(2-amino-3-imidazol-4-ylpropanamido)-2-methoxycarbonylethyl)phenoxy)benzyl]thiazolidin-2,4-dione dihydrochloride.

A solution of 5-[4-(4-(2-(2-N-t-butoxycarbonylamino-3-imidazol-4-ylpropanamido-2-methoxycarbonylethyl)phenoxy)benzyl]thiazolidin-2,4-dione (4.5 g, 7.06 mmol) in acetic acid (15 ml) was bubbled with HCl gas at –10° C. for 50 minutes. The excess of HCl gas was removed by nitrogen bubbling and the solvent was removed by distillation to furnish the titled compound (2.4 g, yield 56%).

$^1$HNMR (DMSO-d$_6$, 400 MHz): δ 3.1(m, 6H), 3.6 (d, 3H), 4.2 (d, 1H), 4.5 (m, 1H), 4.9 (d, 1H), 6.9 (m, 4H), 7.2 (m, 4H), 7.4 (s, 1H), 8.4 (bs, 3H), 8.8 (d, 1H), 9.1 (d, 1H), 12.0 (bs, 1H); m/z$^{M+1}$ 538.

EXAMPLE 2

Preparation of 3-{4-[4-(2,4-dioxothiazolidin-5-ylidenemethyl)-phenoxy]-phenyl}-2-[(pyrrolidine-2-carbonyl)-amino]-propionic acid methyl ester Step (i)

Preparation of 2-(2-{4-[4-(2,4-dioxothiazolidin-5-ylidenemethyl)-phenoxy]-phenyl}-1-methoxycarbonylethylcarbamoyl)-pyrrolidine-1-carboxylic acid tert-butyl ester A solution of 5[4-(4-(2-amino-2-methoxycarbonylethyl) phenoxy)benzylidene]thiazolidin-2,4-dione hydrochloride (2.5 g, 5.76 mmol) and N-Boc-pyrolidin-2-carboxylic acid (1.238 g, 5.76 mmol) in dimethyl formamide (25 ml) was stirred for 60 minutes at 0° C. N,N'-Dicyclohexylcarbodiimide (1.423 g, 6.91 mmol) was added to it and stirring was continued for 10 h at ambient temperature. Water (200 ml) was added to the reaction mixture and stirred for 15 minutes. Ethyl acetate (200 ml) was added to the reaction mixture and stirring continued for another 15 minutes. The organic layer was separated, washed with water (75 ml), dried over anhydrous sodium sulphate and concentrated to afford the crude product, which was purified by column chromatography to furnish the required product (1.1 g, yield 32.4%).

$^1$HNMR (CDCl$_3$, 400 MHz): δ 1.3 (s, 9H), 1.9 (m, 2H), 2.2 (m, 2H), 3.0 (m, 2H), 3.4 (m, 2H), 3.7 (d, 3H), 4.3 (m, 1H), 4.7 (s, 1H), 7.0 (m, 4H), 7.2(m, 2H), 7.4 (m, 2H), 7.8 (s, 1H), 8.8 (s, 1H); m/z$^{M+1}$ 596.2.

Step (ii):

Preparation of 3-{4-[4-(2,4-dioxothiazolidin-5-ylidenemethyl)-phenoxy]-phenyl}-2-[(pyrrolidine-2-carbonyl)-amino]-propionic acid methyl ester To a solution of 5-[4-(4-(2-(N-t-butoxycarbonyl-2-pyrrolidine carbonamide-2-methoxycarbonylethyl)phenoxy)benzylidene]thiazolidin-2,4-dione.(0.5 g, 0.8403 mmol) in dichloromethane (35 ml) was bubbled dry HCl gas at –10° C. for 1 h. The excess of HCl gas was removed by N$_2$ bubbling and concentrated to give the required product (0.35 g, Yield 78%) $^1$HNMR (DMSO-d$_6$, 400 MHz): δ 2.0 (m, 2H), 2.9 (m, 2H), 3.1 (m, 2H), 3.3 (m, 2H), 3.7 (m, 3H), 4.5 (m, 1H), 4.7 (m, 1H), 7.0 (m, 4H), 7.2 (m, 2H), 7.4 (m, 2H), 7.7 (s, 1H); 8.2 (bs, 1H), 11.0 (bs, 1H), 12.0 (bs, 1H); m/z$^{M+1}$ 496.2.

EXAMPLE 3

Preparation of 3-{4-[4-(2,4-dioxothiazolidin-5-ylmethyl)-phenoxy]-phenyl}-2-[(pyrrolidine-2-carbonyl)-amino]-propionic acid methyl ester Step (i)

Preparation of 2-(2-{4-[4-(2,4-dioxothiazolidin-5-ylmethyl)-phenoxy]-phenyl}-1-methoxycarbonylethylcarbamoyl)-pyrrolidine-1-carboxylic acid tert-butyl ester A solution of 5-[4-(4-(2-amino-2-methoxycarbonylethyl) phenoxy)benzyl]thiazolidin-2,4-dione hydrochloride (2.03 g, 4.65 mmol) and N-t-butoxycarbonylpyrrolidin-2-carboxylic acid (1 g, 4.65 mmol) in N,N-dimethylformamide (20 ml) was stirred for 1 h at 0° C. N,N'-Dicyclohexylcarbodiimide (0.96 g, 4.65 mmol) was added to this solution and stirring was continued for 2 h at ambient temperature. Water (150 ml) was added to the reaction mixture, stirred for 20 minutes, ethyl acetate (200 ml) was added and stirring continued for another 15 minutes. The organic layer was separated and washed with water (100 ml), dried over anhydrous sodium sulfate and concentrated to give the crude compound, which was purified by column chromatography (1.42 g, yield 51.2%).

$^1$HNMR (DMSO-d$_6$, 400 MHz): δ 1.3 (s, 9H), 1.8 (m, 2H), 2.3 (m, 3H), 2.9 (m, 1H), 3.1 (m, 2H), 3.2 (m, 2H), 3.6 (s, 3H), 4.1 (m, 1H), 4.5 (m, 1H), 4.9 (t, 1H), 6.9 (m, 4M), 7.2 (m, 4H), 8.2 (d, 1H), 12.0 (s, 1H); m/z$^{M+1}$ 598.3.

Step (ii)

Preparation of 3-{4-[4-(2,4-dioxothiazolidin-5-ylmethyl)-phenoxy]-phenyl}-2-[(pyrrolidine-2-carbonyl)-amino]-propionic acid methyl ester A solution of 5-[4-(4-(2-(N-t-butoxycarbonyl-2-pyrrolidinecarboxamido-2-methoxy carbonylethyl)phenoxy)benzyl] thiazolidin-2,4-dione (1.1 g, 1.83 mmol) in dichloromethane (20 ml) was bubbled with HCl gas at –10° C. for 50 minutes. The excess HCl gas was removed by N$_2$ bubbling and concentrated to furnish the title compound (0.75 g, yield 76%).

$^1$HNMR (DMSO-d$_6$, 400 MHz): δ 1.9 (m, 2H), 2.3 (m, 3H), 2.9 (m, 1H), 3.1 (m, 1H), 3.2 (m, 2H), 3.6 (d, 3H), 4.1 (m, 1H), 4.5 (m, 1H), 4.7 (dd, 1H), 4.8(t, 1H), 6.9 (m, 4H), 7.2 (m, 4H), 8.2 (d, 1H), 8.8 (bs, 1H), 12.0 (bs, 1H); m/z$^{M+1}$ 498.2.

EXAMPLE 4

Preparation of 5-[4-(4-(2-(2-aminopropanamido)-2-methoxycarbonylethyl)phenoxy)benzyl]thiazolidin-2,4-dione hydrochloride.

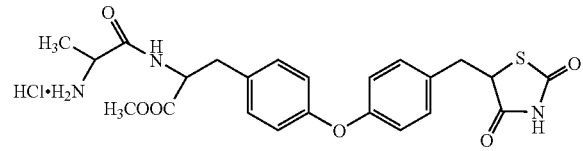

Step (i)

Preparation of 5-[4-(4-(2-(2-t-Butoxycarbonylaminopropanamido)-2-methoxy carbonylethyl)phenoxy)benzyl]thiazolidin-2,4-dione.

A solution of 5-[4-(4-(2-amino-2-methoxycarbonylethyl)phenoxy)benzyl]thiazolidin-2,4-dione hydrochloride (2.3 g, 5.27 mmol) and 2-t-butoxycarbonylaminopropionic acid (0.997 g, 5.27 mmol) in tetrahydrofuran (20 ml) was stirred for 1 h at 0° C. N,N'-Dicyclohexylcarbodiimide (1.086 g, 5.27 mmol) was added to this solution and stirring was continued for 1.5 h at ambient temperature. Water (200 ml) was added to the reaction mixture, stirred for 15 minutes, ethyl acetate (250 ml) was added and stirring was continued for another 15 minutes. The organic layer was separated and washed with water (100 ml), dried over anhydrous sodium sulfate and concentrated to give the title compound, which was purified by column chromatography (0.7 g, yield 23%).

$^1$HNMR (DMSO-$d_6$, 400 MHz): δ 1.0 (d, 3H), 1.3 (s, 9H), 2.9 (m, 3H), 3.5 (d, 3H), 4.0 (m, 1H), 4.4 (m, 1H), 4.8 (t, 1H), 6.9 (m, 4H), 7.2 (m, 4H), 8.2 (dd, 1H), 12.0 (s, 1H), 12.4 (bs, 1H); m/z$^{M+1}$ 572.5.

Step (ii)

5-[4-(4-(2-(2-Aminopropanamido)-2-methoxycarbonylethyl)phenoxy)benzyl]thiazolidin-2,4-dione hydrochloride A solution of 5-[4-(4-(2-(2-t-butoxycarbonylaminopropanamido)-2-methoxycarbonyl ethyl)phenoxy)benzyl]thiazolidin-2,4-dione (1 g, 1.75 mmol) in dichloromethane (10 ml) was bubbled with HCl gas at −10° C. for 50 minutes. The excess HCl gas was removed by N$_2$ bubbling and concentrated to dryness to afford the title compound (0.59 g, yield 66.3%).

$^1$HNMR (DMSO-$d_6$, 400 MHz): δ 1.1 (d, 1H), 1.3 (m, 2H), 2.9 (m, 2H), 3.0 (m, 1H), 3.7 (d, 3H), 3.9 (s, 1H), 4.5 (m, 1H), 4.8 (t, 1H), 6.9 (m, 4H), 7.2 (m, 4H), 8.1 (bs, 2H), 8.4 (bs, 1H), 8.8 (m, 1H), 12.0 (s, 1H); m/z$^{M+1}$ 472.2.

EXAMPLE 5

Preparation of 5-[4-(4-(2-(2-aminopropanamido)-2-methoxycarbonylethyl)phenoxy)benzylidene]thiazolidin-2,4-dione hydrochloride.

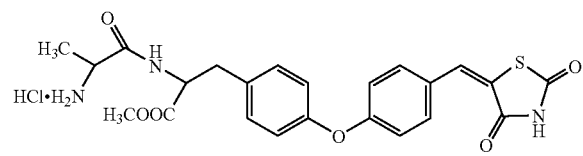

Step (i)

5-[4-(4-(2-(2-t-Butoxycarbonylaminopropanamido)-2-methoxycarbonylethyl)phenoxy)benzylidene]thiazolidin-2,4-dione A solution of 5-[4-(4-(2-amino-2-methoxycarbonylethyl)phenoxy)benzylidene]thiazolidin-2,4-dione hydrochloride (2 g, 4.6 mmol) and 2-t-butoxycarbonylamino propionic acid (0.87 g, 4.6 mmol) in dimethyl formamide (10 ml) was stirred for 1 h at 0° C. N,N'-Dicyclohexylcarbodiimide (1.139 g, 5.5 mmol) was added to this solution and stirring was continued for 2 h at ambient temperature. Water (200 ml) was added to the reaction mixture, stirred for 15 minutes, ethyl acetate (250 ml) added and stirring was continued for another 15 minutes. The organic layer was separated and washed with water (100 ml), dried over anhydrous sodium sulfate and concentrated to furnish the crude compound which was purified by column chromatography (0.95 g, yield 36.3%).

$^1$HNMR (CDCl$_3$, 400 MHz): δ 1.3 (d, 3H), 1.4 (s, 9H), 3.1 (m, 1H), 3.2 (m, 1H), 3.7 (s, 3H), 4.2 (bs, 1H), 4.9 (m, 1H), 5.1 (m, 1H), 6.6 (m, 1H), 7.0 (m, 4H), 7.1 (m, 2H), 7.4 (m, 2H), 7.8 (s, 1H), 8.0 (s, 1H), 9.3 (bs, 1H); m/z$^{M+1}$ 570.2.

Step (ii)

5-[4-(4-(2-(2-aminopropanamido)-2-methoxycarbonylethyl)phenoxy)benzylidene]thiazolidin-2,4-dione hydrochloride.

A solution of 5-[4-(4-(2-(2-t-butoxycarbonylaminopropanamido)methoxycarbonylethyl)phenoxy)benzylidene]thiazolidin-2,4-dione (0.5 g, 0.878 mmol) in dichloromethane (10 ml) was bubbled with HCl gas at −10° C. for 40 minutes. The excess of HCl gas was removed by N$_2$ bubbling and the solvent was removed by distillation to give the title compound (0.39 g, yield 87.8%).

$^1$HNMR (DMSO-$d_6$, 400 MHz): δ 1.3 (d, 3H), 3.0 (m, 2H), 3.6 (m, 3H), 3.7 (m, 1H), 7.0 (m, 4H), 7.3 (m, 2H), 7.6 (m, 2H), 7.8 (s, 1H), 8.2 (m, 3H), 8.9 (m, 1H) 12.6 (s, 1H); m/z$^{M+1}$ 470.1.

EXAMPLE 6

Preparation of 5-[4-(4-(2-(2-aminoacetamido)-2-methoxycarbonylethyl)phenoxy)benzylidene]thiazolidin-2,4-dione hydrochloride.

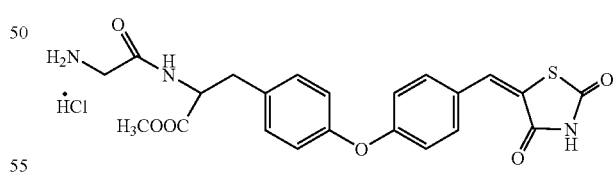

Step (i)

5-[4-(4-(2-(2-t-Butoxycarbonylaminoacetamido)-2-methoxycarbonylethyl)phenoxy)benzylidene]thiazolidin-2,4-dione A solution of 5-[4-(4-(2-amino-2-methoxycarbonylethyl)phenoxy)benzylidene]thiazolidin-2,4-dione hydrochloride (3.28 g, 7.56 mmol) and N-2-t-butoxycarbonyl aminoacetic acid (1.32 g, 7.56 mmol) in tetrahydrofuran (25 ml) was stirred for 45 minutes at 0° C. N,N'-Dicyclohexylcarbodiim ide (1.87 g, 9.08 mmol) was added to this solution and stirring was continued for 1.5 h at ambient temperature. Water (150 ml) was added to the reaction mixture and stirred for 20 minutes. Ethyl acetate (200 ml) was added to the reaction mixture and stirring continued for another 15 minutes. The organic layer was separated and washed with water (100 ml), dried over anhydrous sodium sulfate and concentrated to give the crude compound, which was purified by column chromatography (2.8 g, yield 66.8%).

$^1$HNMR (CDCl$_3$, 400 MHz): δ 1.4 (s, 9H), 3.1 (m, 2H), 3.7 (s, 3H), 3.8 (m, 2H), 3.9 (m, 1H), 4.9 (t, 1H), 5.1 (s, 1H), 6.6 (d, 1H), 7.0 (m, 4H), 7.2 (m, 2H), 7.4 (m, 2H), 7.8 (s, 1H), 8.7 (bs, 1H); m/z$^{M+1}$ 556.2.

Step (ii)

Preparation of 5-[4-(4-(2-(2-aminoacetamido)-2-methoxycarbonylethyl)phenoxy)benzylidene]thiazolidin-2,4-dione hydrochloride A solution of 5-[4-(4-(2-(2-t-butoxycarbonylaminoacetamido)-2-methoxy-carbonylethyl)phenoxy)benzylidene]thiazolidin-2,4-dione (2.8 g, 5.05 mmol) in dichloromethane (30 ml) was bubbled with HCl gas at −10° C. for 1 h. The excess HCl gas was removed by N$_2$ bubbling and the solvent was removed by distillation to give the title compound (2.01 g, yield 81%).

$^1$HNMR (DMSO-d$_6$, 400 MHz): δ 2.9 (m, 1H), 3.0 (m, 1H), 3.5 (m, 2H), 3.6 (s, 3H), 4.0 (t, 1H), 7.0 (m, 4H), 7.2 (m, 2H), 7.5 (m, 2H), 7.7 (s, 1H), 8.1 (bs, 3H), 8.96 (d, 1H); m/z$^{M+1}$ 456.1.

(4.02 g, 2.29 mmol) in tetrahydrofuran (20 ml) was stirred for 40 minutes at 0° C. N,N'-Dicyclohexylcarbodiimide (0.57 g, 2.75 mmol) was added to this solution and stirring was continued for 2 h at ambient temperature. Water (200) ml was added to the reaction mixture and stirred for 20 minutes. Ethyl acetate (250 ml) was added to the reaction mixture and stirring continued for another 15 minutes. The organic layer was separated and washed with water (100 ml), dried over anhydrous sodium sulfate, concentrated and purified by column chromatography to give the title compound (0.75 g, 59.1%).

$^1$HNMR (CDCl$_3$, 400 MHz): δ 1.4 (s, 9H), 3.1 (m, 3H), 3.5 (d, 1H), 3.7 (s, 3H), 3.8 (m, 2H), 4.5 (t, 1H), 4.8 (d, 1H), 5.1 (d, 1H), 6.5 (d, 1H), 6.9 (m, 4H), 7.1 (m, 2H), 7.3 (m, 2H), 8.2 (bs, 1H); m/z$^{M+1}$ 558.2.

Step (ii)

5-[4-(4-(2-(2-Aminoacetamido)-2-methoxycarbonylethyl) phenoxy)benzyl]thiazolidin-2,4-dione hydrochloride A solution of 5-[4-(4-(2-(2-t-butoxycarbonylaminoacetamido)-2-methoxycarbonylethyl) phenoxy)benzyl]thiazolidin-2,4-dione (0.73 g, 1.31 mmol) in dichloromethane (30 ml) was bubbled with HCl gas at −10° C. for 1.25 h. The excess HCl gas was removed by N$_2$ bubbling and the solvent was removed by distillation to provide the title compound (0.51 g, yield 78.8%).

$^1$HNMR (DMSO-d$_6$, 400 MHz: δ 2.9 (m, 1H), 3.1 (m, 2H), 3.2 (m, 1H), 3.5 (d, 2H), 3.6 (s, 3H), 4.5 (t, 1H), 4.8 (t, 1H), 6.9 (m, 4H), 7.2 (m, 4H), 8.0 (bs, 3H), 8.92 (d, 1H); m/z$^{M+1}$ 458.3.

EXAMPLE 8

Preparation of 5-[4-(4-(2-(4-methylthio-2-aminobutyramido)-2-methoxycarbonyl ethyl)phenoxy) benzylidene]thiazolidin-2,4-dione hydrochloride

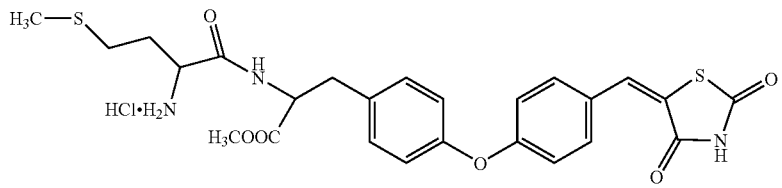

EXAMPLE 7

Preparation of 5-[4-(4-(2-(2-aminoacetamido)-2-methoxycarbonylethyl)phenoxy)benzyl]thiazolidin-2,4-dione hydrochloride.

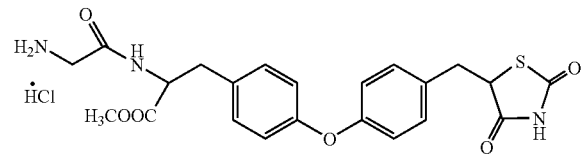

Step (i)

5-[4-(4-(2-(2-t-Butoxycarbonylaminoacetamido)-2-methoxycarbonylethyl)phenoxy)benzyl]thiazolidin-2,4-dione A solution 5-[4-(4-(2-amino-2-methoxycarbonylethyl) phenoxy)benzyl]thiazolidin-2,4-dione hydrochloride (1 g, 2.29 mmol) and N-2-t-butoxycarbonylamino acetic acid Step (i)

5-[4-(4-(2-(4-Methylthio-2-t-butoxycarbonylaminobutyramido)-2-methoxycarbonyl ethyl)phenoxy)benzylidene]thiazolidin-2,4-dione A solution of 5-[4-(4-(2-amino-2-methoxycarbonylethyl) phenoxy)benzylidene]thiazolidin-2,4-dione hydrochloride (3.08 g, 7.09 mmol) and N-2-t-butoxycarbonylamino-4-methylthiobutyric acid (1.77 g, 7.09 mmol) in 1,4-dioxan (50 ml) was stirred for 30 minutes at 0° C. N,N'-Dicyclohexylcarbodiimide (1.75 g, 8.51 mmol) was added to this solution and stirring was continued for 2 h at ambient temperature. Water (250 ml) was added to the reaction mixture and stirred for 20 minutes. Ethyl acetate (250 ml) was added to the reaction mixture and stirring continued for another 15 minutes. The organic layer was separated and washed with water (100 ml), dried over anhydrous sodium sulfate, concentrated and purified by column chromatography to give the title compound (1.89 g, 42.4%).

$^1$HNMR (CDCl$_3$, 400 MHz): δ 1.4 (s, 9H), 1.8 (m, 2H), 2.0 (s, 3H), 2.5 (m, 2H), 3.0 (m, 1H), 3.2 (m, 1H), 3.7 (s, 3H), 4.3 (d,

1H), 4.8 (m, 1H), 5.3 (dd, 1H), 7.0 (m, 4H), 7.2 (m, 2H), 7.4 (m, 2H), 7.8 (s, 1H), 9.0 (bs, 1H); m/z$^{M+1}$ 630.2.

Step (ii)

5-[4-(4-(2-(4-Methylthio-2-aminobutyramido)-2-methoxycarbonylethyl)phenoxy)benzylidene]thiazolidin-2,4-dione hydrochloride.

A solution of 5-[4-(4-(2-(4-methylthio-2-t-butoxycarbonylaminobutyramido)-2-methoxy carbonylethyl)phenoxy) benzylidene]thiazolidin-2,4-dione (1.38 g, 2.2 mmol) in dichloromethane (30 ml) was bubbled with HCl gas at −10° C. for 80 minutes. The excess HCl gas was removed by $N_2$ bubbling and the solvent was removed by distillation to furnish the title compound (1 g, yield 80.6%).

$^1$HNMR (DMSO-d$_6$, 400 MHz): δ 1.7 (s, 1H), 1.9 (s, 3H), 2.0 (s, 2H), 3.0 (m, 3H), 3.6 (dd, 3H), 3.8 (m, 1H), 4.6 (m, 1H), 7.0 (m, 4H), 7.3 (m, 2H), 7.6 (m, 2H), 7.7 (s, 1H), 8.3 (d, 2H), 9.0 (m, 1H), 12.5 (bs, 1H); m/z$^{M+1}$ 530.3.

EXAMPLE 9

Preparation of 5-[4-(4-(2-(4-methylthio-2-aminobutyramido)-2-methoxycarbonyl ethyl)phenoxy)benzyl]thiazolidin-2,4-dione hydrochloride.

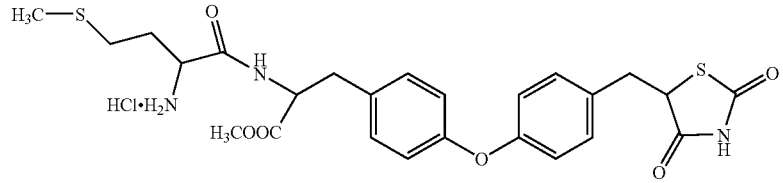

Step (i)

5-[4-(4-(2-(4-Methylthio-2-t-butoxycarbonylaminobutyramido)-2-methoxycarbonyl ethyl)phenoxy)benzyl]thiazolidin-2,4-dione.

A solution of 5-[4-(4-(2-amino-2-methoxycarbonylethyl) phenoxy)benzyl]thiazolidin-2,4-dione hydrochloride (1.5 g, 3.44 mmol) and N-2-t-butoxycarbonylmethionine (0.86 g, 3.44 mmol) in tetrahydrofuran (20 ml) was stirred for 45 minutes at 0° C. N,N'-Dicyclohexylcarbodiimide (0.85 g, 4.12 mmol) was added to this solution and stirring was continued for 1.5 hours at ambient temperature. Water (200) ml was added to the reaction mixture and stirred for 15 minutes. Ethyl acetate (250 ml) was added to the reaction mixture and stirring continued for another 15 minutes. The organic layer was separated and washed with water (100 ml), dried over anhydrous sodium sulfate, concentrated and purified by column chromatography to afford the title compound (1 g, yield 47.6%).

$^1$HNMR (CDCl$_3$, 400 MHz): δ 1.4 (s, 9H), 1.9 (m, 1H), 2.0 (s, 5H), 2.5 (m, 2H), 3.1 (m, 3H), 3.5 (m, 1H), 3.7 (s, 3H), 4.3 (m, 1H), 4.5 (t, 1H), 4.8 (d, 1H), 5.2 (d, 1H), 6.9 (m, 4H), 7.0 (m, 2H), 7.19 (m, 2H), 9.0 (bs, 1H); m/z$^{M+1}$ 632.3.

Step (ii)

5-[4-(4-(2-(4-Methylthio-2-aminobutyramido)-2-methoxycarbonylethyl)phenoxy) benzyl]thiazolidin-2,4-dione hydrochloride A solution of 5-[4-(4-(2-(4-methylthio-2-t-butoxycarbonylaminobutyramido)-2-methoxycarbonylethyl)phenoxy) benzyl]thiazolidin-2,4-dione (1 g, 1.58 mmol) in dichloromethane (30 ml) was bubbled with HCl gas at 20° C. for 30 minutes. The excess HCl gas was removed by $N_2$ bubbling and the solvent was removed by distillation to furnish the title compound (0.8 g, yield 89.2%).

$^1$HNMR (DMSO-d$_6$, 400 MHz): δ 1.7 (m, 1H), 1.9 (s, 3H), 2.1(s, 2H), 2.9 (m, 2H), 3.1 (m, 2H), 3.6 (d, 3H), 3.8 (m, 1H), 4.5 (m, 1H), 4.9 (t, 1H), 6.9 (m, 4H), 7.2 (m, 4H), 8.2 (bs, 3H), 9.0 (m, 1H), 12.1 (bs, 1H); m/z$^{M+1}$ 532.2.

Protocols Used for Biological Testing and the Biological Data

The compounds of the present invention have been tested for lowering blood glucose, in different models for their biological activity.

EXAMPLE 10

Testing hyperglycemia in diabetic db/db mice.

The hypoglycemic effect of compounds A and B have been examined in spontaneous animal models of diabetes, leptin receptor knockout (db/db mice). The db/db mice have defective leptin receptor and show hyperglycemia with significant weight gain. The compound at a dose of 5, 10 (FIGS. 1C, 2C) and 50 mg/kg body weight (FIGS. 1B, 2B) was given orally in these animals for a period of 15-21 days. Treatment of db/db diabetic animals resulted in significant improvements of hyperglycemic conditions. See FIGS. 1A-C and 2A-C. In the time course experiment (Figs 1A and 2A), blood glucose was measured following the oral dose and it showed that there is a significant drop in blood glucose in treated animals compared to control groups (24% and 30%).

EXAMPLE 11

Lowering of Body Weight Gain, Improvement of Food and Water Intake in db/db Mice.

Figure 3B:
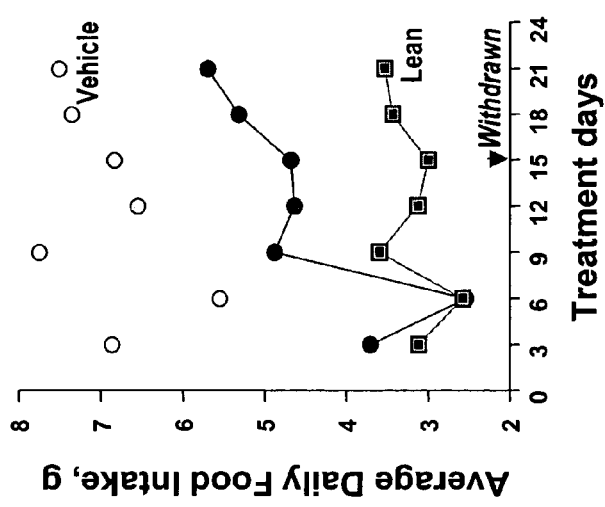
Figure 3C:
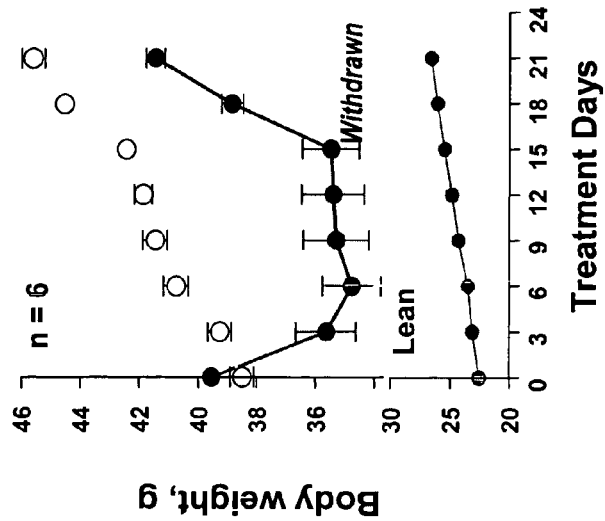

The db/db mice have defective leptin receptor and show hyperglycemia with significant weight gain. The compound B at a dose of 50 mg/kg body weight was given orally in these animals for a period of 15-21 days. Treatment of db/db diabetic animals resulted in significant reductions in body weight gain (FIG. 3A) compared to controls. Both food (FIG. 3B) and water intake (3C) were improved significantly after compound treatment compared to control groups.

EXAMPLE 12

Improvement of HDL Cholesterol and Lowering of LDL, TG and VLDL in db/db Mice.

The leptin knock-out ob/ob mice is also considered a good model for insulin resistance and hyperlipidemia. Treatment of these animals with the compounds A and B lowered serum triglycerides (FIG. 4A) and VLDL (FIG. 4B) concentration by >50%. Similarly, a 19% decrease in serum cholesterol (FIG. 4C) concentrations were observed in 15-day treatment study. Interestingly we found there is an increase of 20-32% HDL (high density lipoprotein) levels compared to vehicle treated animals (FIG. 4D). These results suggest that the compounds in this class have strong anti-lipidemic properties and can improve the sensitivity of insulin.

EXAMPLE 13

Improvement of Hyperglycemia in Diabetic Obese ob/ob Mice.

The hypoglycemic effect of compounds A and B have been examined in spontaneous animal models of obese diabetes (ob/ob) mice, here they do not have any circulating leptin levels. The ob/ob mice is lacking leptin signaling and show hyperglycemia with significant weight gain. The compounds at a dose 50 mg/kg body weight were given orally in these animals for a period of 15-21 days. Treatment of ob/ob diabetic animals resulted in significant improvements of hyperglycemic conditions (FIG. 5A). There was significant improvement of OGTT (oral glucose tolerance) following treatment with both the compounds (FIG. 5B).

EXAMPLE 14

Lowering of Body Weight Gain, Improvement of Food and Water Intake in Obese Diabetic ob/ob Mice.

Figure 6C:
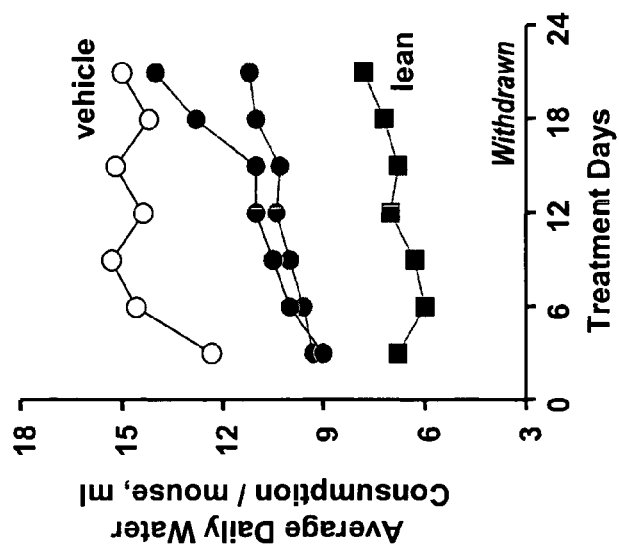
FIGS. 6A-C show the effect on weight (FIG. 6A), food (FIG. 6B) and water intake (FIG. 6C) in ob/ob mice of Compounds A and B.
Figure 6B:
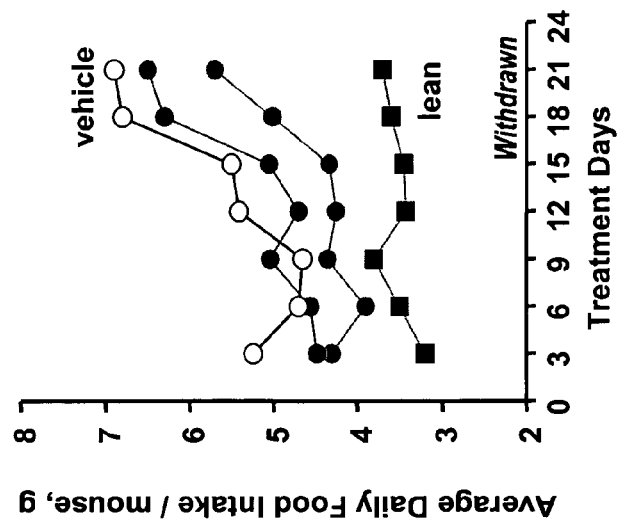
Figure 6A:
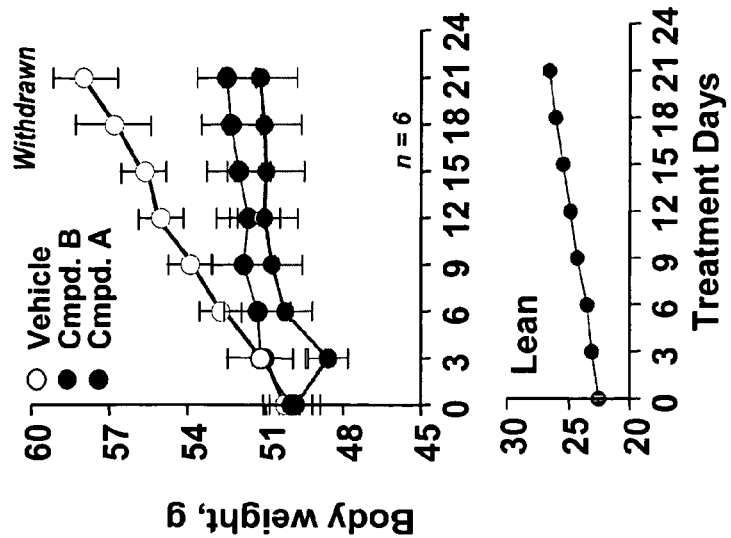

The ob/ob mice are lacking circulating leptin r and show hyperglycemia with significant weight gain. Both the compounds A and B at a dose of 50 mg/kg body weight were given orally in these animals for a period of 15-21 days. Treatment of ob/ob diabetic animals resulted in significant reductions in body weight gain compared to controls (FIG. 6A). Both food (FIG. 6B) and water intake (FIG. 6C) were improved significantly after compound treatment compared to control groups.

EXAMPLE 15

Compound A is not an Adipogenic Compound Like Other PPARγ Agonists.

All known TZD or non TZD PPARγ compounds shows lipid accumulation (adipogenesis) in 3T3-L1 fibroblasts. Rosiglitazone and Compound A at 0.1 and 10 uM concentrations, were treated for 7 days and at the end lipid droplets were stained with oil red O and visualized under microscope. Compound A did not show any adipogenesis compared to rosiglitazone. This suggests that the anti-hyperglycemic activity of the compound is not mediated by PPARγ.

EXAMPLE 16

Improvement in Basal Glucose Uptake in 3T3-L1 Adipocytes.

Figure 7:
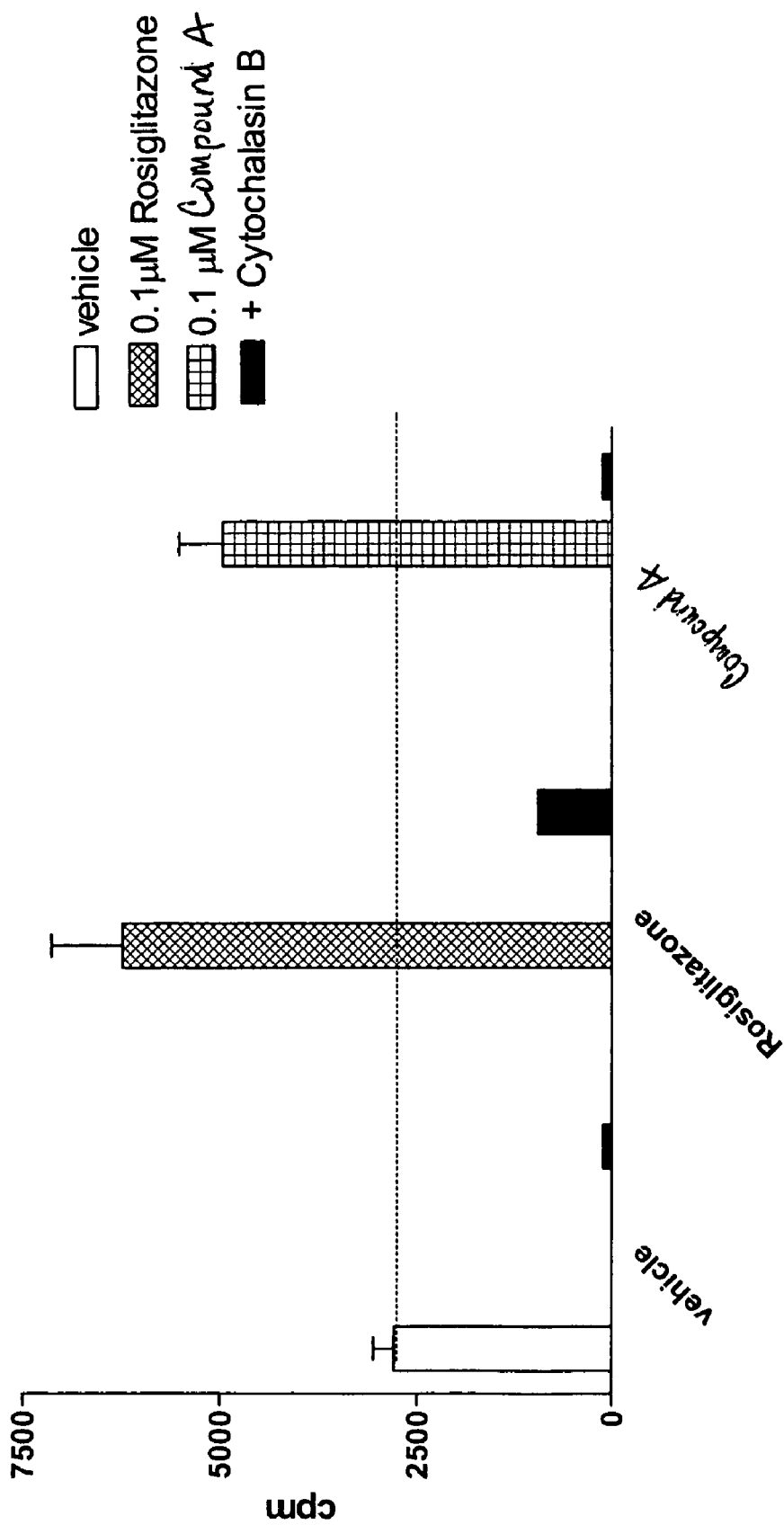
FIG. 7 shows the effect of Compound A in basal glucose uptake in 3T3-L1 adipocytes.

Basal glucose uptake was carried out in 3T3-L1 differentiated adipocytes. After 72 hr of treatment they were challenged with either rosiglitazone or Compound A, then glucose uptake was carried out in absence of insulin. The control was 0.1% DMSO. Cytochalasin B was added in another set of wells to show the effect is receptor mediated. Although less adipogenic Compound A showed significant increase in basal glucose uptake compared to control cells (FIG. 7).

EXAMPLE 17

Inhibition of Major Pro-Inflammatory Cytokines in Human Monocyte Cells

Human THP-1 monocyte cells were cultured and incubated with compounds A and B at different concentrations. Cells were then challenged with lipopolysaccharides (LPS) at a concentration of (1 µg/ml) for 24 hours. Cell supernatants were then analyzed for the presence of TNFα, IL-1β and IL-6 cytokines by antibody directed enzyme-linked immunoassay (FIGS. 8A, 8B, and 8C). The compounds A and B can inhibit the production of three major pro-inflammatory cytokines in a dose dependent manner. No significant change in cell viability (FIG. 8D) was observed with incubation of cells in the presence of highest concentration of the compound. These results strongly suggest that compounds A and B are highly effective in reducing the production of pro-inflammatory cytokines.

The invention claimed is:

1. A method for relieving the clinical symptoms of diabetes comprising administering an effective amount of a compound of formula (I):

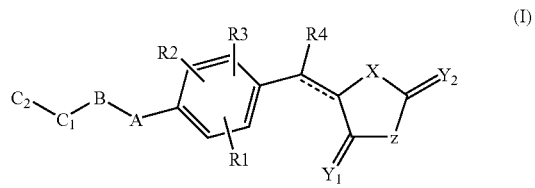

(I)

their analogs, their tautomeric forms, their stereoisomers, their polymorphs, their pharmaceutically acceptable salts, their pharmaceutically acceptable solvates, wherein — represents an optional double bond; X and Z may be same or different and independently represent oxygen, sulfur or $NR_5$, wherein $R_5$ represents hydrogen or linear or branched alkyl group provided both X and Z are not same when they represent oxygen or sulfur; $Y_1$ and $Y_2$ may be same or different and independently represent oxygen, sulfur or $NR_5$, wherein $R_5$ represents hydrogen or linear or branched alkyl group; $R_1$, $R_2$, $R_3$ and $R_4$ may be same or different and independently represent hydrogen, halogen, hydroxy, nitro, cyano, formyl, mono-, di-, or unsubstituted amino, linear or branched alkyl, linear or branched alkoxy group; A represents oxygen, sulfur or NR, wherein R represents hydrogen or linear or branched alkyl; B represents a bond or substituted or unsubstituted aryl, heterocyclyl or heteroaryl ring of 5 to 14 carbon and hetero atoms; $C_1$ and $C_2$ may be same or different and independently represent an amino acid and are linked through —NH— of $C_1$ and —CO— of $C_2$, or through —CO— of $C_1$ and —NH— of $C_2$; B is directly linked or linked through alkyl or alkylene groups of 1 to 4 carbon atoms to the α-carbon of $C_1$; to a patient in need thereof.

2. A method for relieving the clinical symptoms of disorders associated with insulin resistance comprising administering an effective amount of a compound of formula (I):

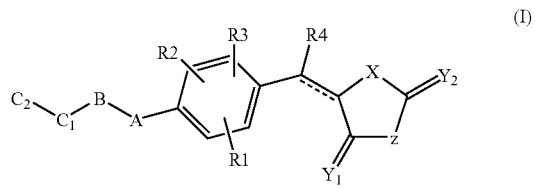

(I)

their analogs, their tautomeric forms, their stereoisomers, their polymorphs, their pharmaceutically acceptable salts, their pharmaceutically acceptable solvates, wherein — represents an optional double bond; X and Z may be same or different and independently represent oxygen, sulfur or $NR_5$, wherein R5 represents hydrogen or linear or branched alkyl group provided both X and Z are not same when they represent oxygen or sulfur; $Y_1$ and $Y_2$ may be same or different and independently represent oxygen, sulfur or $NR_5$, wherein $R_5$ represents hydrogen or linear or branched alkyl group; $R_1$, $R_2$, $R_3$ and $R_4$ may be same or different and independently represent hydrogen, halogen, hydroxy, nitro, cyano, formyl, mono-, di-, or unsubstituted amino, linear or branched alkyl, linear or branched alkoxy group; A represents oxygen, sulfur or NR, wherein R represents hydrogen or linear or branched alkyl; B represents a bond or substituted or unsubstituted aryl, heterocyclyl or heteroaryl ring of 5 to 14 carbon and hetero atoms; $C_1$ and $C_2$ may be same or different and independently represent an amino acid and are linked through —NH— of $C_1$ and —CO— of $C_2$, through —CO— of $C_1$ and —NH— of $C_2$; B is directly linked or linked through alkyl or alkylene groups of 1 to 4 carbon atoms to the α-carbon of $C_1$; to a patient in need thereof.

3. A method according to claim 1, wherein the diabetes is caused by insulin resistance or impaired glucose tolerance.

4. A method according to claim 1, wherein the diabetes is type I or type II.

5. A method for reducing glucose, free fatty acids, cholesterol and triglyceride levels in the plasma comprising administering an effective amount of a compound of formula (I)

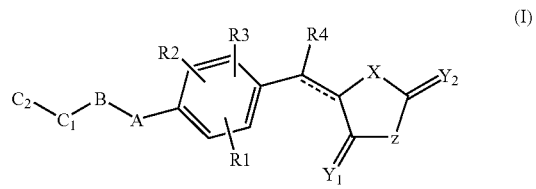

(I)

their analogs, their tautomeric forms, their stereoisomers, their polymorphs, their pharmaceutically acceptable salts, their pharmaceutically acceptable solvates, wherein — represents an optional double bond; X and Z may be same or different and independently represent oxygen, sulfur or $NR_5$, wherein $R_5$ represents hydrogen or linear or branched alkyl group provided both X and Z are not same when they represent oxygen or sulfur; $Y_1$ and $Y_2$ may be same or different and independently represent oxygen, sulfur or $NR_5$, wherein $R_5$ represents hydrogen or linear or branched alkyl group; $R_1$, $R_2$, $R_3$ and $R_4$ may be same or different and independently represent hydrogen, halogen, hydroxy, nitro, cyano, formyl, mono-, di-, or unsubstituted amino, linear or branched alkyl, linear or branched alkoxy group; A represents oxygen, sulfur or NR, wherein R represents hydrogen or linear or branched alkyl; B represents a bond or substituted or unsubstituted aryl, heterocyclyl or heteroaryl ring of 5 to 14 carbon and hetero atoms; $C_1$ and $C_2$ may be same or different and independently represent an amino acid and are linked through —NH— of $C_1$ and —CO— of $C_2$, or through —CO— of $C_1$ and —NH— of $C_2$; B is directly linked or linked through alkyl or alkylene groups of 1 to 4 carbon atoms to the α-carbon of $C_1$; to a patient in need thereof.

6. The method according to claim 1, wherein the group represented by B is aryl selected from the group consisting of phenyl and naphthyl; heteroaryl ring selected from the group consisting of pyridyl, pyrrolyl, thiazolyl, indolyl, imidazolyl and furyl or heterocyclyl ring selected from the group consisting of piperazine, morpholine, piperidine and pyrrolidine.

7. The method according to claim 1, wherein the amino acids represented by $C_1$ and $C_2$ are selected from alanine, glycine, arginine, asparagine, cysteine, cystine, glutamic acid, glutamine, histidine, isoleucine, leucine, lysine, methionine, ornithine, proline, serine, threonine, tryptophan and tyrosine.

8. The method according to claim 7 wherein said compound comprises 5-[4-(4-(2-(2-amino-3-imidazol-4-yl propanamido)-2-methoxy carobonylethyl)phenoxy)benzylidene]thiazolidin-2,4-dione or a salt thereof.

9. The method according to claim 7 wherein said compound comprises 5-[4-(4-(2-(2-amino-3-imizazol-4-ylpropanamido)-2-carboxyethyl)phenoxy)benzyl]thiazolidin-2,4,dione or a salt thereof.

10. The method according to claim 2, wherein the group represented by B is aryl selected from the group consisting of phenyl and naphthyl; heteroaryl ring selected from the group consisting of pyridyl, pyrrolyl, thiazolyl, indolyl, imidazolyl and furyl or heterocyclyl ring selected from the group consisting of piperazine, morpholine, piperidine and pyrrolidine.

11. The method according to claim 2, wherein the amino acids represented by $C_1$ and $C_2$ are selected from alanine, glycine, arginine, asparagine, cysteine, cystine, glutamic acid, glutamine, histidine, isoleucine, leucine, lysine, methionine, ornithine, proline, seine, threonine, tryptophan and tyrosine.

12. The method according to claim 11 wherein said compound comprises 5-[4-(4-(2-(2-amino-3-imidazol-4-yl propanamido)-2-methoxy carobonylethyl)phenoxy)benzylidene]thiazolidin-2,4-dione or a salt thereof.

13. The method according to claim 11 wherein said compound comprises 5-[4-(4-(2-(2-amino-3-imizazol-4-ylpropanamido)-2-carboxyethyl)phenoxy)benzyl]thiazolidin-2,4, dione or a salt thereof.

14. The method according to claim 5, wherein the group represented by B is aryl selected from the group consisting of phenyl and naphthyl; heteroaryl ring selected from the group consisting of pyridyl, pyrrolyl, thiazolyl, indolyl, imidazolyl and furyl or heterocyclyl ring selected from the group consisting of piperazine, morpholine, piperidine and pyrrolidine.

15. The method according to claim 5, wherein the amino acids represented by $C_1$ and $C_2$ are selected from alanine, glycine, arginine, asparagine, cysteine, cystine, glutamic acid, glutamine, histidine, isoleucine, leucine, lysine, methionine, ornithine, proline, serine, threonine, tryptophan and tyrosine.

16. The method according to claim 15 wherein said compound comprises 5-[4-(4-(2-(2-amino-3-imidazol-4-yl propanamido)-2-methoxy carobonylethyl)phenoxy)benzylidene]thiazolidin-2,4-dione or a salt thereof.

17. The method according to claim 15 wherein said compound comprises 5-[4-(4-(2-(2-amino-3-imizazol-4-ylpropanamido)-2-carboxyethyl)phenoxy)benzyl]thiazolidin-2,4, dione or a salt thereof.

* * * * *